US 12,049,611 B2

(12) United States Patent
Oakley et al.

(10) Patent No.: US 12,049,611 B2
(45) Date of Patent: Jul. 30, 2024

(54) CELL CULTURE

(71) Applicant: FIBROFIND IP LIMITED, Tyne and Wear (GB)

(72) Inventors: Fiona Oakley, Newcastle Upon Tyne (GB); Lee Borthwick, Newcastle Upon Tyne (GB); Clive Griffiths, Newcastle Upon Tyne (GB); Michael Drinnan, Newcastle Upon Tyne (GB)

(73) Assignee: FIBROFIND IP LIMITED, Tyne and Wear (GB)

( * ) Notice: Subject to any disclaimer, the term of this patent is extended or adjusted under 35 U.S.C. 154(b) by 397 days.

(21) Appl. No.: 15/770,106

(22) PCT Filed: Oct. 21, 2016

(86) PCT No.: PCT/GB2016/053310
§ 371 (c)(1),
(2) Date: Apr. 20, 2018

(87) PCT Pub. No.: WO2017/068376
PCT Pub. Date: Apr. 27, 2017

(65) Prior Publication Data
US 2019/0002809 A1    Jan. 3, 2019

(30) Foreign Application Priority Data
Oct. 22, 2015    (GB) ...................... 1518767

(51) Int. Cl.
*C12M 1/32* (2006.01)
*B01F 31/23* (2022.01)
(Continued)

(52) U.S. Cl.
CPC ............. *C12M 23/12* (2013.01); *B01F 31/23* (2022.01); *B01L 3/5025* (2013.01); *C12M 27/16* (2013.01);
(Continued)

(58) Field of Classification Search
None
See application file for complete search history.

(56) References Cited

U.S. PATENT DOCUMENTS 5,358,871 A * 10/1994 Stevens ...................... B01L 9/06
                                                                422/943
5,422,270 A *  6/1995 Caspi ....................... C12M 23/12
                                                                435/973
(Continued)

FOREIGN PATENT DOCUMENTS

WO        2002097029 A2    12/2002
WO        2003078565 A1     9/2003
(Continued)

OTHER PUBLICATIONS

Sung. "A microfluidic device for a pharmacokinetic-pharmacodynamic (PK-PD) model on a chip". Lab on a Chip. Jan. 2010 (Year: 2010).*
(Continued)

*Primary Examiner* — Holly Kipouros
*Assistant Examiner* — Nathan G Esperon
(74) *Attorney, Agent, or Firm* — Husch Blackwell LLP

(57) ABSTRACT

Aspects of the present invention relate to apparatus for use in cell and tissue culture techniques. Particularly, although not exclusively, embodiments of the present invention relate to apparatus which contribute to providing a dynamic cell culture environment. Also disclosed herein are methods for culturing cells and/or tissues, together with in vitro methods of testing drug efficacy as well as other subject matter.

13 Claims, 28 Drawing Sheets

(51) Int. Cl.
*B01L 3/00* (2006.01)
*C12M 1/00* (2006.01)
*C12M 1/34* (2006.01)
*C12M 1/42* (2006.01)
*C12M 3/06* (2006.01)
*C12N 5/071* (2010.01)
*G01N 33/50* (2006.01)

(52) U.S. Cl.
CPC ............ *C12M 29/12* (2013.01); *C12M 35/08* (2013.01); *C12M 41/46* (2013.01); *C12N 5/0671* (2013.01); *G01N 33/5014* (2013.01); *G01N 33/5067* (2013.01); *B01L 2300/0829* (2013.01); *B01L 2400/0457* (2013.01); *B01L 2400/0475* (2013.01); *C12N 2527/00* (2013.01)

(56) References Cited

U.S. PATENT DOCUMENTS

| | | | | |
|---|---|---|---|---|
| 5,593,587 | A * | 1/1997 | Fumihiko | C12M 47/02 210/474 |
| 5,652,142 | A * | 7/1997 | Barker | C12M 25/04 435/297.5 |
| 2003/0017582 | A1* | 1/2003 | Kim | G01N 33/5064 435/305.3 |
| 2005/0009179 | A1 | 1/2005 | Gemmiti et al. | |
| 2005/0186669 | A1* | 8/2005 | Ho | C12M 23/14 435/287.1 |
| 2005/0260745 | A1 | 11/2005 | Domansky et al. | |
| 2007/0077181 | A1* | 4/2007 | Youngbear | B01L 3/5085 422/400 |
| 2007/0207537 | A1* | 9/2007 | Cui | C12M 23/34 435/297.5 |
| 2009/0233361 | A1 | 9/2009 | Farhat et al. | |
| 2010/0273258 | A1* | 10/2010 | Lannutti | C12M 35/04 435/366 |
| 2013/0029412 | A1 | 1/2013 | Reis et al. | |
| 2013/0059322 | A1* | 3/2013 | Hung | C12M 25/14 435/29 |
| 2015/0267158 | A1* | 9/2015 | McKim | C12M 21/08 435/297.5 |

FOREIGN PATENT DOCUMENTS

| | | | | |
|---|---|---|---|---|
| WO | 2003083044 | A3 | 10/2003 | |
| WO | WO2003083044 | A2 | 10/2003 | |
| WO | WO2006033935 | A2 | 3/2006 | |
| WO | WO 2006/097749 | | 9/2006 | |
| WO | WO 2007/004699 | | 1/2007 | |
| WO | 2007044699 | A1 | 4/2007 | |
| WO | WO2007044699 | A1 | 4/2007 | |
| WO | WO-2010069080 | A1 * | 6/2010 | ............ B01D 35/30 |
| WO | WO2011135339 | A2 | 11/2011 | |
| WO | 2011161480 | A1 | 12/2011 | |
| WO | WO-2011161480 | A1 * | 12/2011 | ........ B01L 3/502738 |
| WO | WO2014051503 | A1 | 4/2014 | |
| WO | WO2014102527 | A1 | 7/2014 | |
| WO | WO2014111605 | A1 | 7/2014 | |
| WO | WO2014145753 | A1 | 9/2014 | |
| WO | WO2015001321 | A1 | 1/2015 | |
| WO | WO2015004482 | A2 | 1/2015 | |
| WO | 2016166315 | A1 | 10/2016 | |

OTHER PUBLICATIONS

Eppendorf ("Technical Data Sheet, Eppendorf Cell Culture Plate, 6-Well") https://www.eppendorf.com/product-media/doc/en/90656/ Eppendorf_Consumables_Technical-data_Cell-Culture-Plate-6-Well. pdf (Year: 2014).*

Thermo Fisher Scientific ("Useful information for various sizes of cell culture dishes and flasks") https://www.thermofisher.com/us/ en/home/references/gibco-cell-culture-basics/cell-culture-protocols/ cell-culture-useful-numbers.html (Year: 2015).*

Benam et al. "Engineered In Vitro Disease Models," Annual Review of Pathology: Mechanisms of Disease, 2015, Vo. 10, pp. 195-262.

Mazzei, D.; et al. (2010). A low shear stress modular bioreactor for connected cell culture under high flow rates. Biotechnology and Bioengineering, 106(1):127-137.

International Preliminary Report on Patentability issued in PCT/ GB2016/053310, mailed Apr. 24, 2018. 7 pages.

International Search Report and Written Opinion] issued in PCT/ GB2016/053310, mailed Feb. 1, 2017, 12 pages.

Toxicology in vitro, vol. 9, 1995, WR Leeman et al., "Cytotoxicity of retinoic acid, menadione and aflatoxin B(I) in rat liver slices using Netwell inserts as a new culture system", 291-298.

* cited by examiner

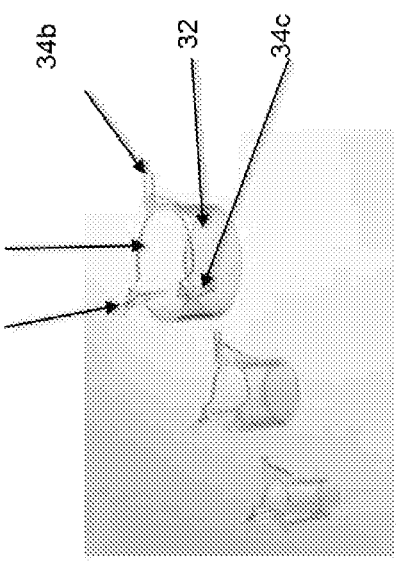
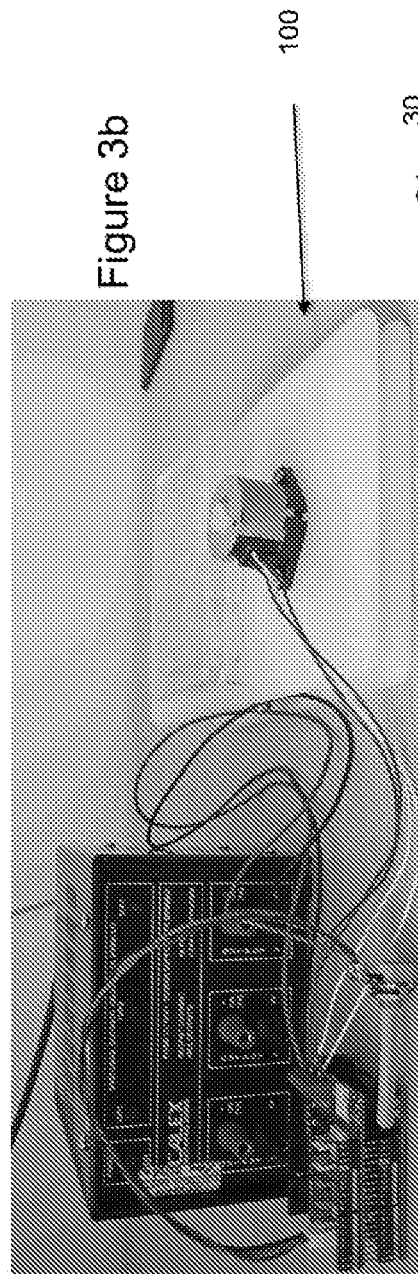
Figure 3b
Figure 4b
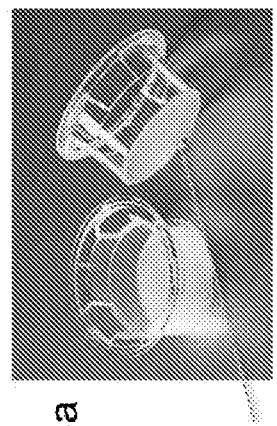
Figure 4a

CELL CULTURE

CROSS-REFERENCE TO RELATED APPLICATIONS

This application is a U.S. National Stage Application of International Patent Application No. PCT/GB2016/053310, filed Oct. 21, 2016, which claims the benefit of Great Britain Patent Application No. 1518767.7, filed Oct. 22, 2015, the disclosures each of which is expressly incorporated by reference in its entirety.

FIELD OF THE INVENTION

Aspects of the present invention relate to apparatus for use in cell and tissue culture techniques. Particularly, although not exclusively, embodiments of the present invention relate to apparatus which contribute to providing a dynamic cell culture environment. Also disclosed herein are methods for culturing cells and/or tissues, together with in vitro methods of testing drug efficacy as well as other subject matter.

BACKGROUND TO THE INVENTION

Cell and tissue culture plays a considerable role in both basic and applied life science research. A standard device used in cell or tissue culture or for performing chemical or cellular assays is the multi-well plate. Multi-well plates are available in a variety of formats. For many general cell culture and tissue engineering applications, 6-, 12-, 24-, 48-, and 96-well formats are most commonly used although higher-density plates, e.g., 384, 1536, or higher are also utilised. Multi-well plates are used in a number of biological assay formats as they are well suited for screening a number of samples simultaneously. Automated laboratory equipment such as plate readers, high throughput screening apparatus and the like has been developed specifically to be used in association with the multi-well format. As a result, the multi-well plate has become a standard format for biological assays.

A disadvantage of using conventional multi-well plates is that the complexity of the physiological environment is not replicated. For example, tissues and organs of the body in vivo are continuously perfused by the blood and lymphatic systems. This perfusion enables constant removal of cell waste products and new nutrients to be provided. Typically static cell culture does not accurately represent this system, even if media is regularly removed and replaced. Furthermore, known multi-well plates do not provide any form of dynamic chemical or physical stimulus such as concentration gradients, flow, pressure or mechanical stress to cells situated in the wells. As a result, in vitro testing using conventional multi-well plates often does not represent in vivo environments.

As a result, there is a growing interest in developing more dynamic culture systems which will enable the environment surrounding the cells or tissue in culture to be altered during the course of experiment.

A number of bioreactors have been designed with an aim to more accurately represent the in vivo environment. These "dynamic" bioreactors are intended to provide more accurate models of human disease on which to test efficacy and toxicity of candidate drug molecules for example.

An example of a bioreactor system which relies on a pumping mechanism is provided by Kirkstall Limited, United Kingdom. This system utilises a plurality of "modular" cell culture chambers, an electronic control circuit and a peristaltic pump which pumps fluid e.g. cell culture media through a chamber.

The field of drug development is an example of a field in which the development of dynamic in vitro systems may be advantageous. Drug development projects are often terminated after expensive human clinical trials when unacceptable side effects, toxicity or lack of therapeutic efficacy are evident. The development of in vitro systems which accurately predict those drugs which will be safe and efficacious in man before in vivo clinical trials are commenced is desired.

A therapeutic area of interest is the development of anti-fibrotic compounds to treat fibrotic disorders. The current gold standard research tools used to understand fibrotic disease and test anti-fibrotic candidate molecules are limited to 2D cultures of scar forming cells and in vivo fibrosis molecules in rodents. These approaches have a number of weaknesses associated with them. Firstly, fibrosis is a complex disorder involving multiple cell types, many of which are lacking in 2D culture systems. Furthermore, pre-clinical rodent models do not accurately represent human disease as they lack some of the important features of human clinical pathology.

Ideally, human organ slices e.g. liver slices would be used in in vitro culture systems. However, techniques which involve the use of organ slices are currently limited due to a limited life span in culture. The life span can be extended using existing dynamic cell culture systems which utilise complex pumping mechanisms to generate fluid movement in the system. However, the existing systems have limitations due to their expense and the time required to set up and run the system. In addition, the number of organ slices which can be cultured simultaneously is limited.

It is an aim of aspects of the present invention to at least partially mitigate the problems associated with the prior art.

It is an aim of certain embodiments of the present invention to provide a cost-effective bioreactor system which is suitable for culturing cells and/or tissues e.g. tissue slices.

It is an aim of certain embodiments of the present invention to provide a system and a method which more accurately reflect the in vivo environment of disease for example.

It is an aim of certain embodiments of the present invention to provide apparatus which utilise small volume of cell culture media.

SUMMARY OF CERTAIN EMBODIMENTS OF THE INVENTION

In a broad aspect of the present invention, there is provided apparatus for culturing cells and/or a tissue, comprising:
  a holder body comprising a plurality of chambers for containing a cell culture media, wherein the holder body comprises at least one fluid communication pathway extending between at least two respective chambers of the plurality of chambers, each fluid communication pathway permitting bi-directional fluid flow between the at least two chambers.

This apparatus may also be referred to as a "culture apparatus" or a multi-well plate. Thus, the culture apparatus described herein may include a multi-well plate. The term "multi-well plate" is known in the art and such plates typically comprise a plurality of chambers or wells.

In a first aspect of the present invention, there is provided an apparatus for providing bi-directional fluid flow, the apparatus comprising:

a culture apparatus for culturing cells and/or a tissue or portion thereof and comprising a holder body, the holder body comprising a plurality of chambers for containing a tissue culture media, and at least one fluid communication pathway extending between at least two respective chambers of the plurality of chambers, each fluid communication pathway permitting bi-directional fluid flow between said at least two chambers, and wherein the apparatus for providing bi-directional fluid flow further comprises:

a holder body support; and at least one drive element arranged to rock a holder body supported via the support to thereby repeatedly raise and lower spaced apart ends of the holder body, wherein the apparatus is configured to repeatedly rock the holder body.

Thus, certain embodiments of the present invention provide a cost-effective, medium- or high-throughput bioreactor system. Aptly, the system introduces bi-directional flow of culture media through chambers of a plate apparatus without the need for a pump. Aptly, the volumes of media needed for the system are small, which may be advantageous for drug discovery.

Thus, in the first aspect of the present invention, the apparatus provided is configured to provide bi-directional fluid flow and which incorporates an apparatus which comprises:

a holder body support; and at least one drive element arranged to rock a holder body supported via the support to thereby repeatedly raise and lower spaced apart ends of the holder body and which may be referred to as a "rocker apparatus".

In certain embodiments, the holder body is separable from the holder body support and/or the at least one drive element. Aptly, the holder body is locatable adjacent to a surface of the holder body support.

Aptly, the chambers are arranged in a regular pattern. Aptly, the chambers are configured to accommodate a cell or tissue culture and a predetermined volume of cell culture media. As referred to herein, the term "tissue" may relate to a tissue portion e.g. an organ slice.

In an embodiment, each chamber of said plurality of chambers comprises a base element and at least one side wall element. Aptly, the fluid communication pathway comprises a through channel extending between a base element or side wall element of a first one of the plurality of chambers to a base element or side wall element of a further one of the plurality of chambers.

Aptly, the fluid communication pathway comprises a through slot extending between a base element or side wall element of a first one of the plurality of chambers to a base element or side wall element of a further one of the plurality of chambers. In certain embodiments, the first chamber is provided adjacent to the further chamber. In certain embodiments, the first chamber and the further chamber are connected via the fluid communication pathway to one or more additional chambers of the plurality of chambers.

In certain embodiments, the holder body comprises a plurality of fluid communication pathways, each fluid communication pathway extending between at least two chambers of the plurality of chambers.

Aptly, each fluid communication pathway of the plurality of fluid communication pathways is substantially parallel to and spaced apart from each other fluid communication pathway.

In certain embodiments, each chamber of the plurality of chambers is configured to accommodate a chamber insert element configured to support a cell scaffold element.

In certain embodiments, each chamber of the plurality of chambers comprises an opening for receiving and/or removing tissue culture media and/or a respective chamber insert element.

In certain embodiments, the apparatus further comprises at least one generally cylindrical chamber insert element which comprises a plurality of radially outwardly extending flanges for supporting the chamber insert element within a respective chamber of the plurality of chambers. In one embodiment, the culture apparatus comprises a plurality of chambers, each chamber comprising an insert element.

Aptly, each respective chamber insert element further comprises a cell scaffold element. Aptly, the cell scaffold element comprises a plurality of pores, said plurality of pores having an average diameter of between about 8 μm to about 150 μm. In certain embodiments, the average pore size may be for example 8 μm, 10 μm, 20 μm, 30 μm, 40 μm, 50 μm, 60 μm, 70 μm, 80 μm, 90 μm, 100 μm or 150 μm. In certain embodiments, the pores have an average diameter of between about around 8 μm to about 100 μm. Aptly, the pores are provided on a lower surface of the cell scaffold element.

In certain embodiments, the cell scaffold element comprises an inner surface, wherein the inner surface is coated with a biological molecule. The biological molecule may be for example a scaffold protein such as for example collagen.

In certain embodiments, the holder body comprises at least twelve chambers, e.g. 12, 24, 96, or more. In one embodiment, the holder body comprises 24 chambers.

In certain embodiments, the holder body comprises an outer perimeter wall element. Aptly, the outer perimeter wall element comprises a recessed outer edge portion. Aptly, the outer perimeter wall element is a continuous outer perimeter wall element. Aptly, the continuous outer perimeter wall element is planar. That is to say, in certain embodiments, the holder body does not require connection with a pump or tubing and therefore comprises an outer edge region which does not comprise any inlet or outlet elements. Furthermore, the holder body does not contain elements configured for connection with tubing for example.

Aptly the holder body comprises an underside surface which comprises a recessed edge region which is configured to locate with respect to the recessed outer edge portion of a further holder body such that the holder bodies are located in a nested relationship. In certain embodiments, a plurality of holder bodies may be located in a vertical stacked e.g. nested relationship.

Aptly, the holder body consists essentially of the plurality of chambers, at least one fluid communication pathway, an outer perimeter wall element, wherein each one of said plurality of chambers is connected via a web of material.

In certain embodiments, the holder body is composed of a material selected from polystyrene, polycarbonate, polyethylene, polypropylene, PMMA, cellulose acetate, ZEONEX™, cyclin olefin polymer (COP), ZEONOR™ cyclin olefin polymer (COP), and glass.

In certain embodiments, each respective chamber of the plurality of chambers has a depth of between about 16 mm and 19 mm, e.g. 16 mm, 16.5 mm, 17 mm, 17.5 mm, 18 mm, 18.5 mm or 19 mm.

In an embodiment, the channel has a width of approximately 1.5 mm to 3.5 mm e.g. approx. 2 mm. In one embodiment, the channel has a length of between about 3 mm to about 5 mm. In one embodiment, the channel has a length of approx. 3.5 mm to approx. 4 mm.

In certain embodiments, each chamber may have a depth of between about 16 mm and 19 mm, e.g. 16 mm, 16.5 mm, 17 mm, 17.5 mm, 18 mm, 18.5 mm, or 19 mm. In one embodiment, the chamber has a depth of approximately 18 mm. In one embodiment, the chamber has a depth of approximately 16.5 mm.

In certain embodiments, the culture apparatus further comprises a lid element which is removably positionable over the holder body, the lid element providing a substantially planar cover extending over the plurality of chambers.

In certain embodiments, the plurality of chambers are arranged in rows and columns in a respective orthogonal relationship within the holder body.

In certain embodiments, the culture apparatus may be stackable relative to at least one other culture apparatus.

Aptly, the holder body support comprises a pivot element about which the holder body is rocked. In certain embodiments, the apparatus comprises a platform element supported by the holder body support, the platform element being configured to retain the holder body in a fixed location during rocking. In certain embodiments, the platform element is configured to support and/or retain a plurality of holder bodies in a fixed location during rocking. Aptly, the plurality of holder bodies is retained in a side-by-side arrangement adjacent an upper surface of the platform element. In certain embodiments, the apparatus comprises a plurality of holder bodies in a vertically stacked arrangement.

In certain embodiments, the drive element is configured to rock the holder body at a speed of approximately 1 minute to 20 minutes per complete rocking motion.

In certain embodiments, the drive element comprises a linear actuator. Aptly, the platform element comprises a first end region and a further end region spaced apart from the first end region, and wherein the linear actuator is located at either the first end region or the further end region.

In certain embodiments, the apparatus further comprises a base element, wherein the base element comprises a groove into which the pivot element is locatable.

In certain embodiments neither the culture apparatus nor the rocker apparatus comprise a pump for forcing fluid flow between adjacent chambers.

In a further aspect of the present invention, there is provided an apparatus for repeatedly rocking a holder body, said holder body comprising a plurality of chambers for containing a cell or tissue culture media, wherein the holder body comprises at least one fluid communication pathway extending between at least two respective chambers of the plurality of chambers, each fluid communication pathway permitting bi-directional fluid flow between said at least two chambers, said apparatus comprising:
 a holder body support; and
 at least one drive element arranged to rock a holder body supported via the support to thereby repeatedly raise and lower spaced apart ends of the holder body.

In a further aspect of the present invention, there is provided an in vitro method of culturing cells and/or a tissue or portion thereof, the method comprising:
 a) providing a culture apparatus as described herein; and
 b) for a predetermined period of time, applying a rocking motion to the culture apparatus.

In a further aspect of the present invention, there is provided an in vitro method of culturing cells and/or a tissue or portion thereof comprising:
 a) providing an apparatus according to the first aspect of the present invention; and
 b) for a predetermined period of time, applying a rocking motion to the culture apparatus.

In certain embodiments, the method further comprises locating at least one cell in at least one chamber of the plurality of chambers. Aptly, the method further comprises locating a tissue portion comprising the at least one cell in at least one chamber of the plurality of chambers.

In certain embodiments, the method comprises locating the tissue portion by locating at least one chamber insert element supporting the tissue portion in the at least one chamber of the holder body. Aptly the at least one cell is provided in a cell culture.

In certain embodiments, the cell culture is supported by a cell scaffold element, and the method further comprises locating the cell culture by locating at least one chamber insert element accommodating the cell scaffold element in the at least one chamber of the holder body.

In certain embodiments, the at least one cell is selected from eukaryotic cells and prokaryotic cells, e.g. plant cells, mammalian cells, yeast cells, fungal cells and/or bacterial cells. Aptly, the at least one cell is a mammalian cell selected from epithelial cells, tumour cells, hepatocytes, fibroblast cells, stem cells, myocardiocytes, kidney cells, lung cells, neuronal cells, adipocytes, intestinal cells, skin cells, and immune cells, either alone or in combination.

Aptly the at least one cell is comprised within a tissue portion e.g. an organ slice. Aptly, the tissue portion is sourced from a tissue selected from a lung, a liver, a kidney, a heart, a brain, skin, a pancreas. In certain embodiments, the cell culture and/or tissue portion comprises a plurality of cell types.

In certain embodiments, the at least one chamber is a first one of the plurality of chambers and further wherein the first chamber is connected to at least one further chamber of the plurality of chambers via a fluid communication pathway extending there between, the fluid communication pathway permitting bi-directional fluid flow between the first chamber and further chamber.

Aptly, the chamber insert element comprises a base surface comprising a plurality of pores. Aptly, the plurality of pores are configured to allow bidirectional flow of fluid cell culture media therethrough.

In certain embodiments, the method comprises:
 providing a fluid cell culture media to the first and/or further chamber and;
 applying the rocking motion for a predetermined period of time such that the fluid cell culture media repeatedly flows from the at least one chamber to a further one of the plurality of the chambers and back again.

Aptly, the method comprises providing between about 0.5 ml to 5 ml e.g. 0.5 ml, 0.75 ml, 1 ml, 1.25 ml, 1.5 ml, 1.75 ml, 2 ml, 2.25 ml, 2.5 ml, 3 ml, 3.25 ml, 3.5 ml, 3.75 ml, 4 ml, 4.25 ml, 4.5 ml, 4.75 ml or 5 ml of the fluid cell culture media per chamber to the first and/or further chamber of the plurality of chambers.

Aptly, the method comprises providing between about 1.5 ml to 4 ml of the fluid cell culture media per chamber to the first and/or further chamber of the plurality of chambers. In certain embodiments, the amount of fluid cell culture media added to each chamber will be dependent of the size of the chamber and/or the size of pore provided by a cell scaffold insert.

In certain embodiments, the method further comprises locating a cell culture, wherein the cell culture is seeded with at least one cell, and a cell scaffold element in at least two chambers of the plurality of chambers, and wherein the cell culture located in a first respective chamber is seeded with cells of the same or different cell type to the cell culture located in a further respective chamber.

In certain embodiments, the method comprises;
locating a culture apparatus as described herein to be supported by a platform element of an apparatus according to a first aspect of the present invention;
providing a driving force to the drive element; and
repeatedly raising and lowering spaced apart ends of the holder body so as to apply a rocking motion to the holder body.

In certain embodiments, the method comprises applying a rocking motion for at least 24 hours, e.g. 48 hours, 72 hours, or more.

Aptly, the method further comprises determining viability or other measurable parameter of the cell(s) in the cell culture. Aptly, the or each cell culture comprises hepatocytes, and further wherein the step of determining cell viability or other measurable parameter comprises measuring production of albumin by the cell(s) of the cell culture(s).

In certain embodiments, the method comprises locating a plurality of culture apparatus to be supported by the platform element of the rocker apparatus. Aptly, the method comprises locating the plurality of culture apparatus to be supported in a side-by-side arrangement on an upper surface of the platform element.

In a still yet further aspect of the present invention, there is provided a method of in vitro testing liver toxicity of an agent comprising:
a) providing a culture apparatus according to an aspect of the invention;
b) locating a cell culture or a tissue or portion thereof comprising at least one hepatocyte, and a cell scaffold element to at least one chamber of the plurality of chambers;
c) adding at least one agent to be tested to said at least one chamber;
d) for a predetermined period of time, applying a rocking motion to the apparatus; and
e) monitoring at least one effect of the agent on the hepatocyte.

In a still yet further aspect of the present invention, there is provided a method of in vitro testing liver toxicity of an agent comprising:
a) providing an apparatus according to the first aspect of the invention;
b) locating a cell culture or a tissue or portion thereof comprising at least one hepatocyte, and a cell scaffold element to at least one chamber of the plurality of chambers;
c) adding at least one agent to be tested to said at least one chamber;
d) for a predetermined period of time, applying a rocking motion to the apparatus; and
e) monitoring at least one effect of the agent on the hepatocyte.

In certain embodiments, monitoring at least one effect of the agent comprises monitoring the effect of the agent on the proliferation and/or differentiation and/or function of the hepatocyte as a measure of toxicity of the agent.

Aptly, the hepatocyte is comprised in a liver slice. The hepatocyte cells may be human or non-human. The hepatocytes cells e.g. the liver slice may comprise primary hepatocyte cells. Alternatively or in addition, the hepatocyte cells e.g. the liver slice may comprise non-primary hepatocyte cells e.g. stem cell derived hepatocytes or progenitor cell derived hepatocytes. The hepatocyte cells may be freshly-derived from a patient or donor or multiple donors or from a cryopreserved source.

The method may comprise adding cell culture media to the chamber. The method may also comprise adding the agent to the hepatocyte positioned within a chamber. A combination of agents may be added. The agent may be for example a drug candidate.

In a further aspect of the present invention, there is provided a method of in vitro modelling of tissue disease comprising:
a) providing a culture apparatus according to an aspect of the invention;
b) locating a tissue portion, the tissue portion comprising at least one cell, and a cell scaffold element to at least one chamber of the plurality of chambers;
c) for a predetermined period of time, applying a rocking motion to the culture apparatus; and
d) monitoring at least one characteristic of the tissue portion.

In a further aspect of the present invention, there is provided a method of in vitro modelling of tissue disease comprising:
a) providing an apparatus according to a first aspect of the invention;
b) locating a tissue portion, the tissue portion comprising at least one cell, and a cell scaffold element to at least one chamber of the plurality of chambers;
c) for a predetermined period of time, applying a rocking motion to the culture apparatus; and
d) monitoring at least one characteristic of the tissue portion.

Aptly, the disease is a cancer. Aptly, the disease is fibrosis. Aptly, the tissue disease is a fibrotic disease e.g. lung fibrosis, kidney fibrosis or liver fibrosis. Aptly, the tissue disease is a liver disease.

Aptly, the tissue portion is a liver slice, a kidney slice and/or a lung slice. In certain embodiments, the method comprises determining activation of a cell type within the tissue portion. Aptly, the method comprises determining activation of hepatic myofibroblasts in a tissue portion. Aptly, the method comprises identifying a marker of hepatic myofibroblasts. Aptly, the marker is α-smooth muscle actin.

In certain embodiments, the method comprises determining expansion of a cell type which is associated with a disease state. Aptly, the tissue slice is a liver portion and the method comprises determining expansion of ductular cells. Aptly, the method comprises a step of histological analysis of the tissue portion. In certain embodiments, the method comprises determining presence or absence of an immune cell in the tissue portion. Aptly, the immune cell is a Kupffer cell.

In certain embodiments, the method comprises locating the tissue portion and the cell culture scaffold element by locating at least one chamber insert element supporting a cell culture scaffold element holding a tissue portion in said at least one chamber of the holder body.

In certain embodiments, the method further comprises adding one or more cells to the chamber. Aptly, the one or more cells are immune cells. In certain embodiments, the method comprises adding one or more cancer cells to the chamber.

In certain embodiments, the method comprises locating the cell culture and the cell culture scaffold element by locating at least one chamber insert element supporting a cell culture scaffold element holding a cell culture in said at least one chamber of the holder body.

In certain embodiments, the method further comprises:
adding a fluid cell culture media to said at least one chamber of the plurality of chambers and;
applying the rocking motion for a predetermined period of time such that the fluid cell culture media repeatedly flows from said chamber to a further one of the plurality of the chambers and back again.

Aptly, the method further comprises;
locating a culture apparatus on a platform element of the apparatus according to of the first aspect of the invention;
providing a driving force to the drive element; and
repeatedly raising and lowering spaced apart ends of the holder body so as to apply a rocking motion to the holder body.

In a further aspect of the present invention, there is provided an insert element for supporting a cell and/or tissue portion, wherein the insert element is generally cylindrical and comprises a plurality of radially outwardly extending flanges for supporting the chamber insert element within a respective chamber of an apparatus as described herein, and further wherein respective chamber insert element further comprises a cell scaffold element comprising a plurality of pores, said plurality of pores having an average diameter of between about around 8 µm to about 150 µm.

Aptly, the plurality of pores has an average diameter of from about around 8 µm to about 100 µm.

Certain embodiments of the present invention may provide an in vitro model of liver. In vitro models of liver are an important tool in pharmaceutical drug development and in understanding liver pathophysiology. Certain embodiments of the present invention provide a system which more accurately models organ fibrosis and which may be used to test anti-fibrotic candidate molecules.

In certain embodiments, the apparatus and method is for modelling a liver related disease. Many people with cirrhosis and other liver related disease conditions experience no symptoms in the early stages of the disease. However, as scar tissue replaces healthy tissue, liver functions begin to fail and a person may experience fatigue, exhaustion, loss of appetite, nausea, weakness and loss of weight. As the disease progresses, complications may develop as a result of the loss of liver functions.

As used herein, the term "liver related disease" may refer to one or more diseases, conditions or symptoms or susceptibility to diseases, conditions or symptoms that involve directly or indirectly, the liver, the biliary ducts, the hepatic ducts, the cystic ducts or the gallbladder including the following: acute liver failure, Alagille syndrome, Alcoholic Liver disease, Alpha 1-antitrypsin deficiency, autoimmune hepatitis, biliary atresia, chronic hepatitis, cirrhosis, cholestatic liver disease, cystic disease of the liver, fatty liver, galactosemia, gallstones, Gilbert's syndrome, hemochromatosis, hepatitis A, hepatitis B, hepatitis C, liver cancer, neonatal hepatitis, Non-Alcohol Related Fatty Liver disease, non-alcoholic steatohepatitis, porphyria, primary biliary cirrhosis, primary sclerosing cholangitis, Reye's syndrome, sarcoidosis, steatohepatitis, tyrosinemia, type I glycogen storage disease, viral hepatitis and/or Wilson's disease.

In certain embodiments, the method is a method of modelling fatty liver disease. Fatty liver disease may be Non-Alcohol Related Fatty Liver Disease (NAFLD) or Alcoholic Liver Disease and may be characterised by an inappropriate build up of fat in a subject's liver. Over time, the build up of fat may result in inflammation of the liver and fibrosis.

NAFLD may lead to Non-Alcohol Steatohepatitis (NASH). Thus, in certain embodiments, the method is a method of modelling NASH and/or a progression from NAFLD to NASH.

In certain embodiments, the method of modelling fatty liver disease comprises adding one or more lipids to the tissue portion. Aptly, the one or more lipid is selected from palmitic acid, oleic acid and linoleic acid and combinations thereof. Aptly, the lipid is conjugated to Bovine Serum Albumin (BSA). Aptly, the method comprises culturing the tissue portion with the one or more lipids for up to four days, e.g. 1, 2, 3 or 4 days.

In certain embodiments, the method comprises culturing the tissue portion with a fibrosis-stimulating factor such as for example transforming growth factor-β (tgfb), platelet derived growth factor-bb (pdgf-bb). Aptly, the method comprises the step of culturing the tissue portion with the fibrosis-stimulating factor for up to 4 days e.g. 1, 2, 3 or 4 days.

In certain embodiments, the method comprises culturing the tissue portion with an inflammatory mediator. Aptly, the inflammatory mediator is selected from a pathogen-associated molecular patterns (PAMPs) e.g. lipopolysaccharide (LPS) or poly IC and damage associated molecular (DAMPs) e.g. apoptotic or damaged cells. Aptly, the step of culturing the tissue portion with the inflammatory mediator for up to 4 days e.g. 1, 2, 3 or 4 days.

In certain embodiments, the method comprises culturing the tissue portion with a hepatotoxic agent e.g. e.g. acetaminophen (which causes liver failure) or bile acids (which cause biliary disease) for up to but not limited to 4 days.

In certain embodiments, one or more stimulating agents may be added to the tissue portion. For example, the method may comprise adding one or more of a lipid, an inflammatory agent and a fibrotic stimulating agent. The one or more stimulating agents may be as described herein.

In certain embodiments, the method comprises maintaining the tissue portions standard normoxic tissue culture conditions (21% oxygen, 5% carbon dioxide and 74% nitrogen). In certain embodiments, e.g. to mimic hypoxic injury that occurs during tissue fibrosis and cancer, the tissue portions may be maintained as low as 0.1% oxygen (hypoxia).

Existing in vitro models which utilise human organ slices in culture have limited value due to a rapid loss of organ function in culture. For example, liver slices culture on TRANSWELL® permeable supports have a lifespan of 2 days to 3 days due to hypoxia and degradation of the tissue. An example of a dynamic incubation system for testing cytotoxicity of certain compounds is described in Leeman et al, Toxic. In Vitro, Vol. 9, No. 3, pp. 291-298. However, this system 30 does not provide bi-directional flow between adjacent chambers. Results reported by Leeman et al suggests that cell viability decreases rapidly after 72 hours. Leeman et al also used a high (40%) oxygen concentration during culture.

As a result, liver slices currently have limited value in drug discovery. In contrast to the prior art, certain embodiments of the present invention may be suitable to extend the lifespan of liver slices in culture and therefore improve their usefulness in the testing of candidate drug molecules and modelling of disease e.g. liver-related disorders as detailed above, including for example fibrotic disease of the liver.

In addition, certain embodiments of the present invention may provide a cost-effective, small or medium throughput bioreactor system which more accurately represents in vivo environments including for example disease states.

Furthermore, certain embodiments of the present invention may provide a 3D dynamic model of human or animal disease which can be used to test candidate molecules. Certain embodiments of the present invention provide apparatus and bioreactor systems which enable the viability of cells and/or tissues in culture to be improved.

Particularly, certain embodiments enable the length of cell viability e.g. hepatocyte viability to be extended to 72 hours or more. As a result, the apparatus, systems and methods described herein can be used to maintain cell and tissues for a sufficient length of time to test candidate compound efficacy and the like.

DETAILED DESCRIPTION OF EMBODIMENTS OF THE INVENTION

Embodiments of the present invention will now be described hereinafter, by way of example only, with reference to the accompanying drawings in which:

"CMR" refers to a bidirectional system according to certain embodiments of the present invention.

"CMR2" refers to a bidirectional system according to certain embodiments of the present invention.

Figure 3A:
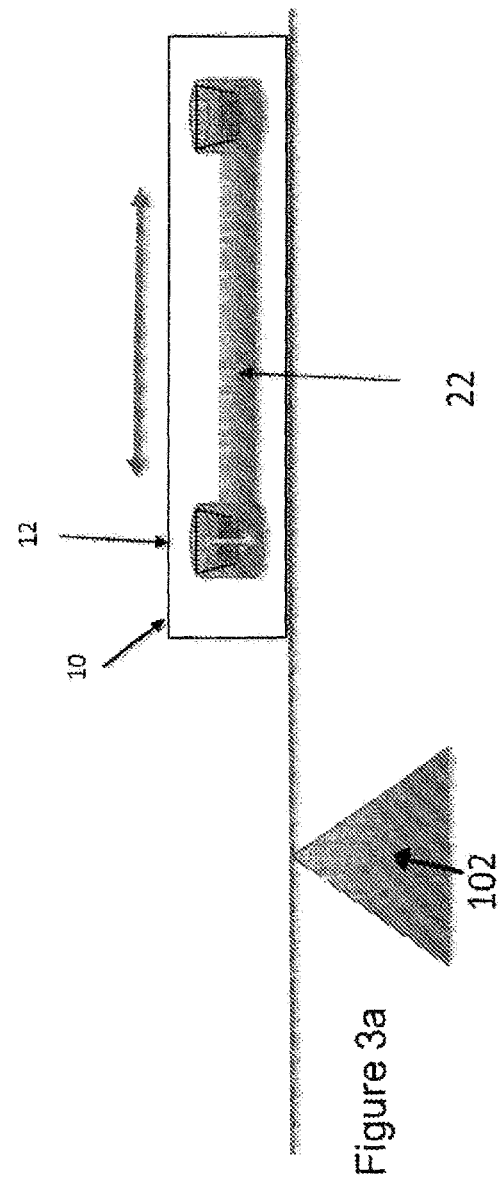

FIG. 3a is a schematic representation of the rocket apparatus holding a multi-well plate apparatus according to certain embodiments of the present invention. As illustrated by arrows, media exchange may occur via insert pores within wells of the plate apparatus. In addition, media exchange may occur via a channel between wells.

Figure 5:
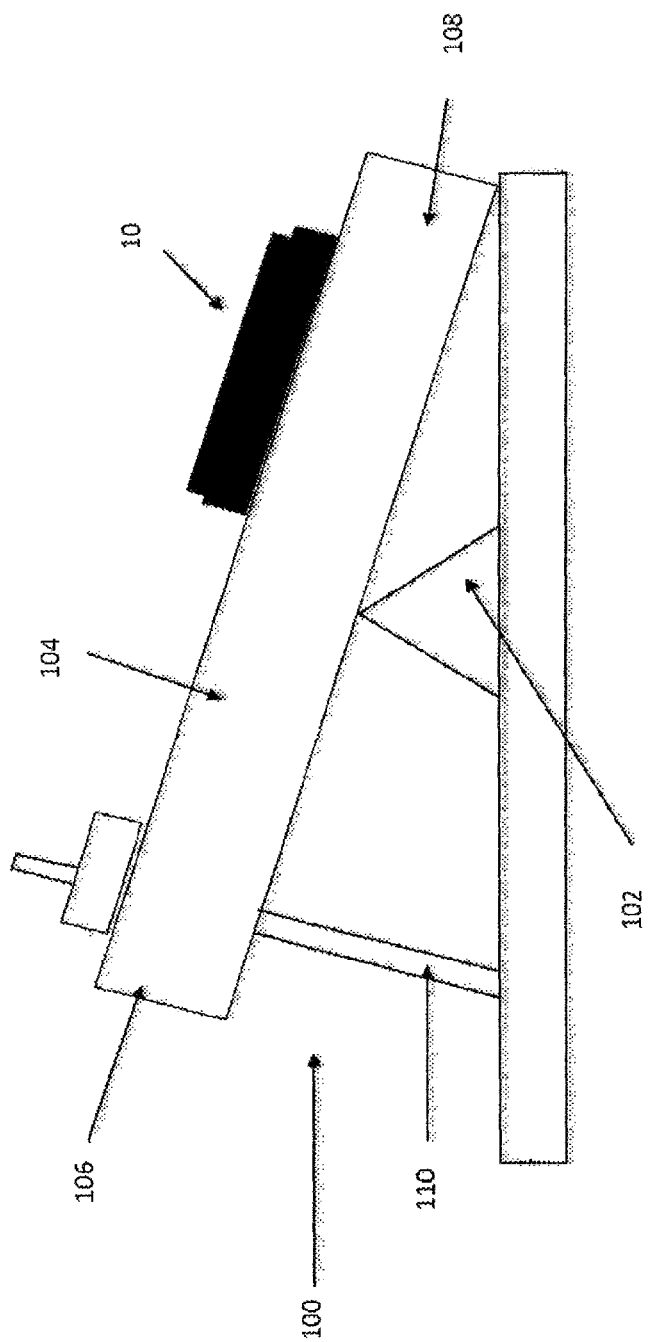
Figure 6:
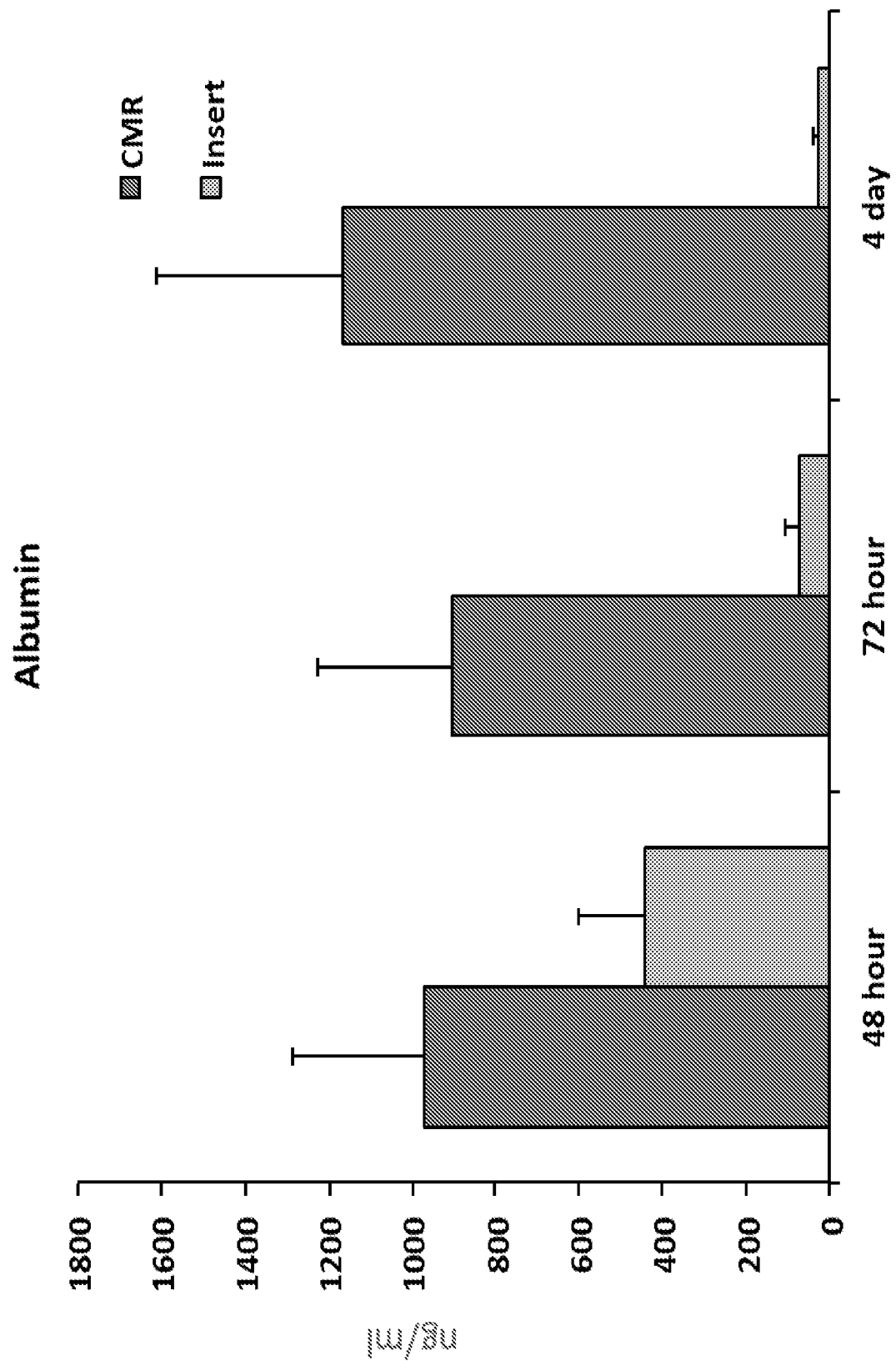

FIG. 3b illustrates a rocker apparatus ("CMR") according to certain embodiments of the present invention;

FIGS. 4a and 4b illustrates a cell scaffold insert element for use in certain embodiments of the present invention;

FIG. 5 is a schematic representation of the rocker apparatus of FIG. 3;

FIG. 6 is a graph illustrating a comparison of albumin production (ng/ml) using a 12 chambered apparatus as described herein (herein referred to as "CMR") as compared to albumin production using a static TRANSWELL® permeable support insert (referred to as "insert") of precision cut liver slices. The viability of the cells is increased using the apparatus of embodiments of the invention. N=8. The left hand bars represent the use of the apparatus of embodiments of the present invention whilst the right hand bars illustrate the static TRANSWELL® permeable support insert. The data shows that the apparatus of certain embodiments maintains the ability of the slice to synthesize and secrete albumin for up to 4 days, which is suggestive of an improved liver function and extended longevity of the tissue slice. Rocking the bioreactor plate promotes media exchange between the two chambers connected by the channel. Each chamber contains an insert, which holds the tissue slice in an inner well. Rocking not only allows media exchange between the two chambers but also permits media exchange via the pores in the culture insert membrane which separate the inner and outer wells. The latter media exchange generates flow around/over the tissue slice, which will aid oxygenation and removal of toxic metabolites, which in turn is likely to increase viability and function (albumin production) of the tissue.

Figure 7:
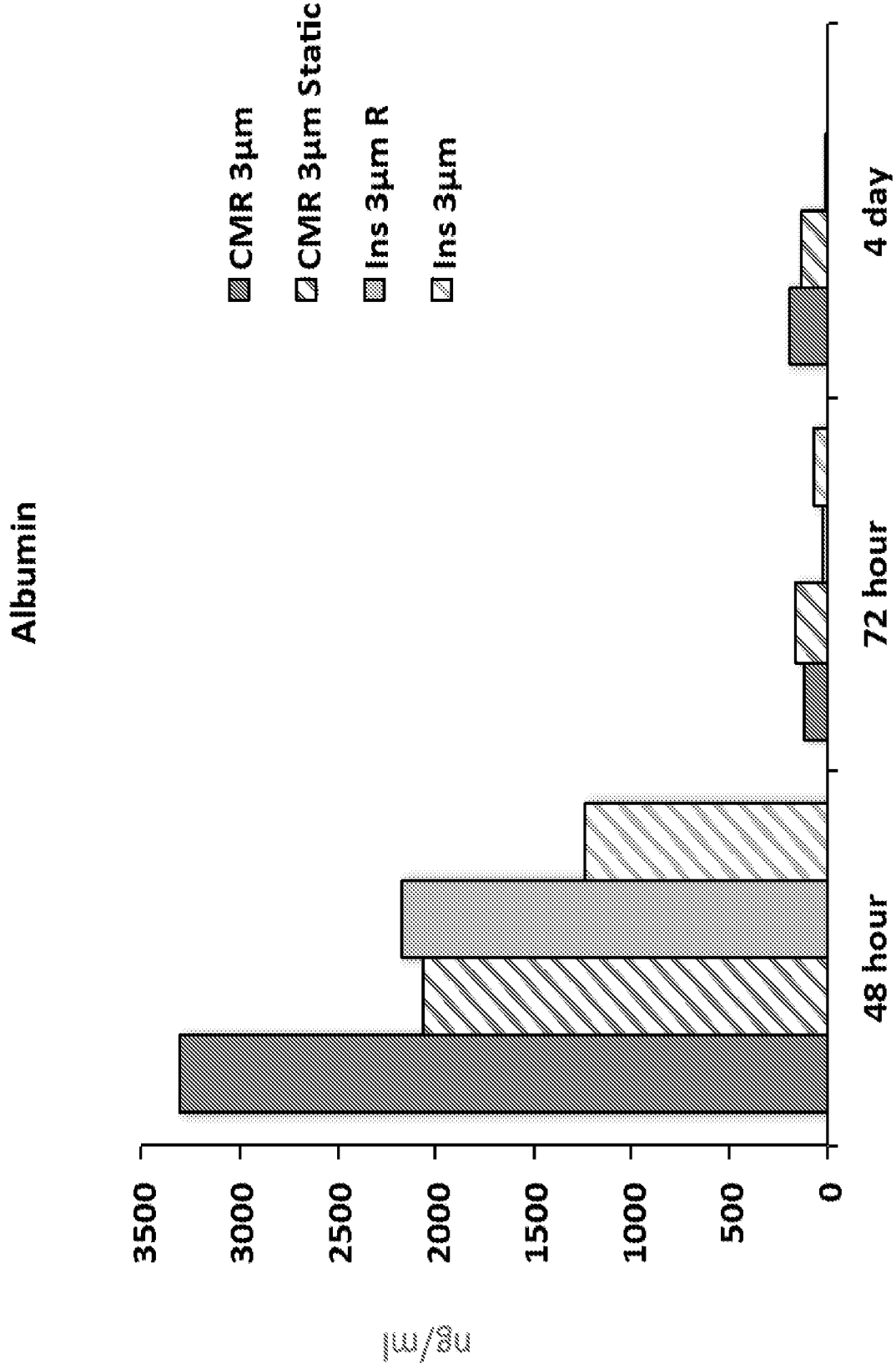
Figure 8:
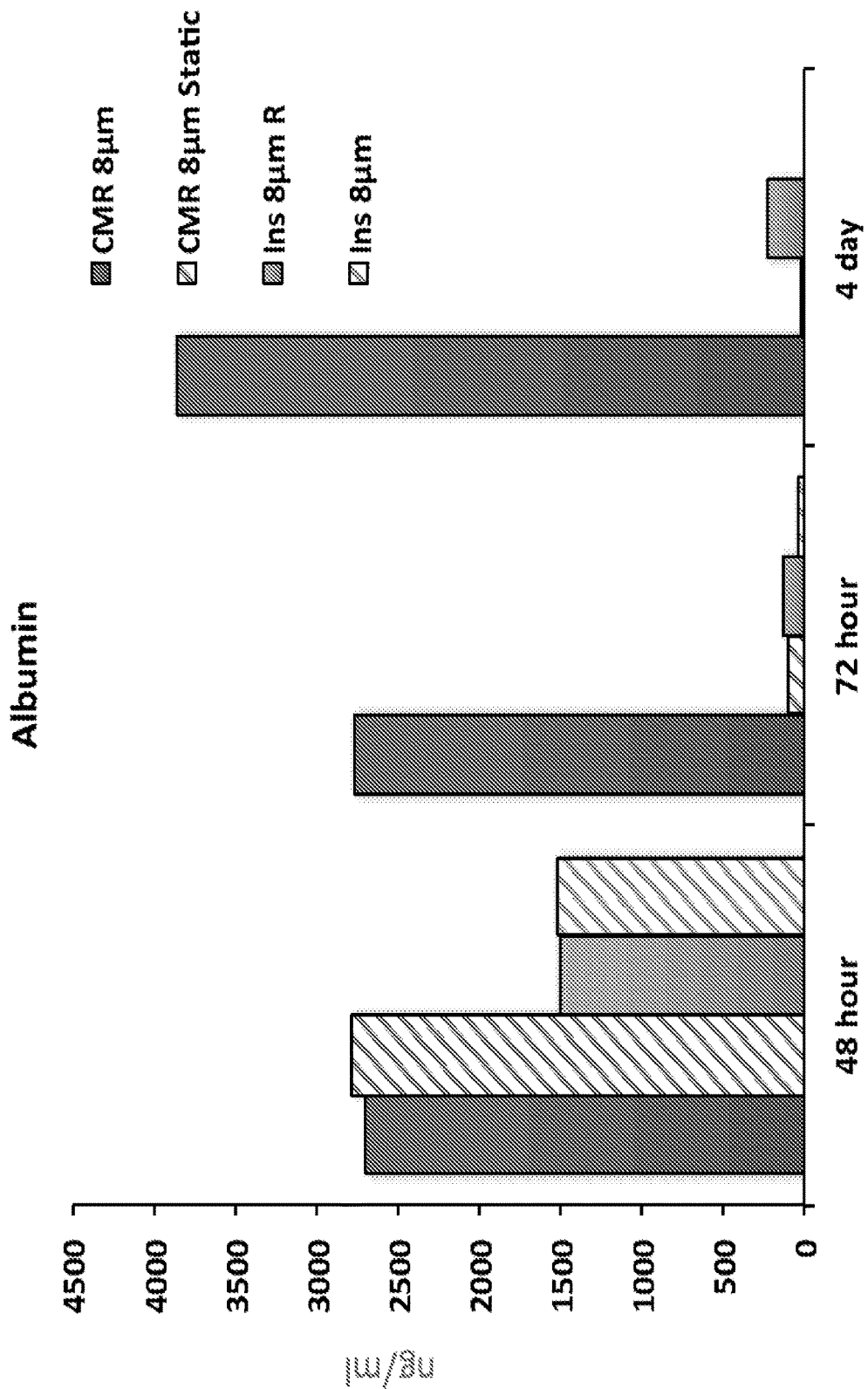

FIG. 7 is a graph illustrating that cell viability and albumin-synthesizing ability using a cell scaffold insert element as described herein having an average membrane pore size of 3 μm are of insufficient size to allow effective media exchange through the insert pore between the inside of the insert and the outer chamber, thus resulting in no improvement in slice function compared to static inserts. "CMR" refers to the use of apparatus of embodiments of the present invention, whilst "Ins" refers to a static (i.e. non-rocking) set-up;

FIG. 8 is a graph illustrating albumin production (ng/ml) from cells cultured using a cell scaffold insert element having an average membrane pore size of 8 μm. 8 μm pore inserts allow effective media exchange through the insert pore between the inside of the insert and the outer chamber, thus resulting in an improvement in slice function compared to static inserts.

Furthermore, rocking of the CMR bioreactor plate ("CMR") retains liver function and albumin secretion. Albumin production is significantly reduced in the static bioreactor plate ("CMR Static"), on static inserts (Ins R), or inserts in standard 12 well plate that are rocked ("Ins"). This suggests that media exchange between the two wells of the chamber in the CMR plate caused by rocking is necessary for retaining albumin secretion.

Figure 9:
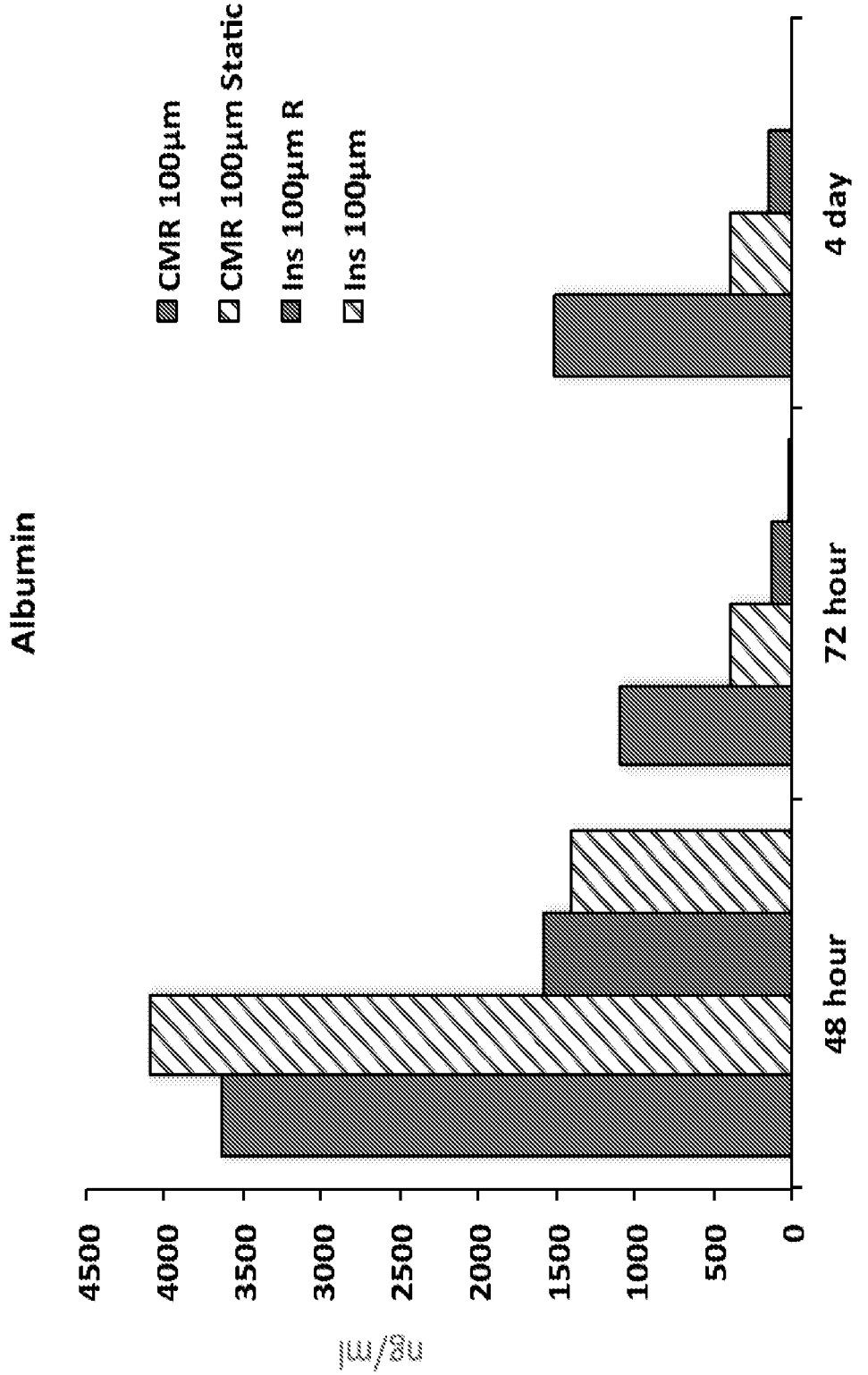

FIG. 9 is a graph illustrating albumin production from cells cultured using a cell scaffold insert element having an average pore size of 100 μm. 100 μm pore inserts provided in an apparatus of certain embodiments (CMR) are of sufficient size to allow effective media exchange through the insert pore between the inside of the insert and the outer chamber, thus resulting in an improvement in slice function compared to static inserts. Again, media exchange between the two wells of the chamber is required to retain albumin secretion ("CMR"). Conversely, albumin production is significantly reduced in the static bioreactor plate with 100 μm insert pores (CMR Static), on static inserts with 100 μm insert pores ("Ins R"), or inserts with 100 μm insert pores in standard 12 well plate that are rocked ("Ins").

Figure 10:
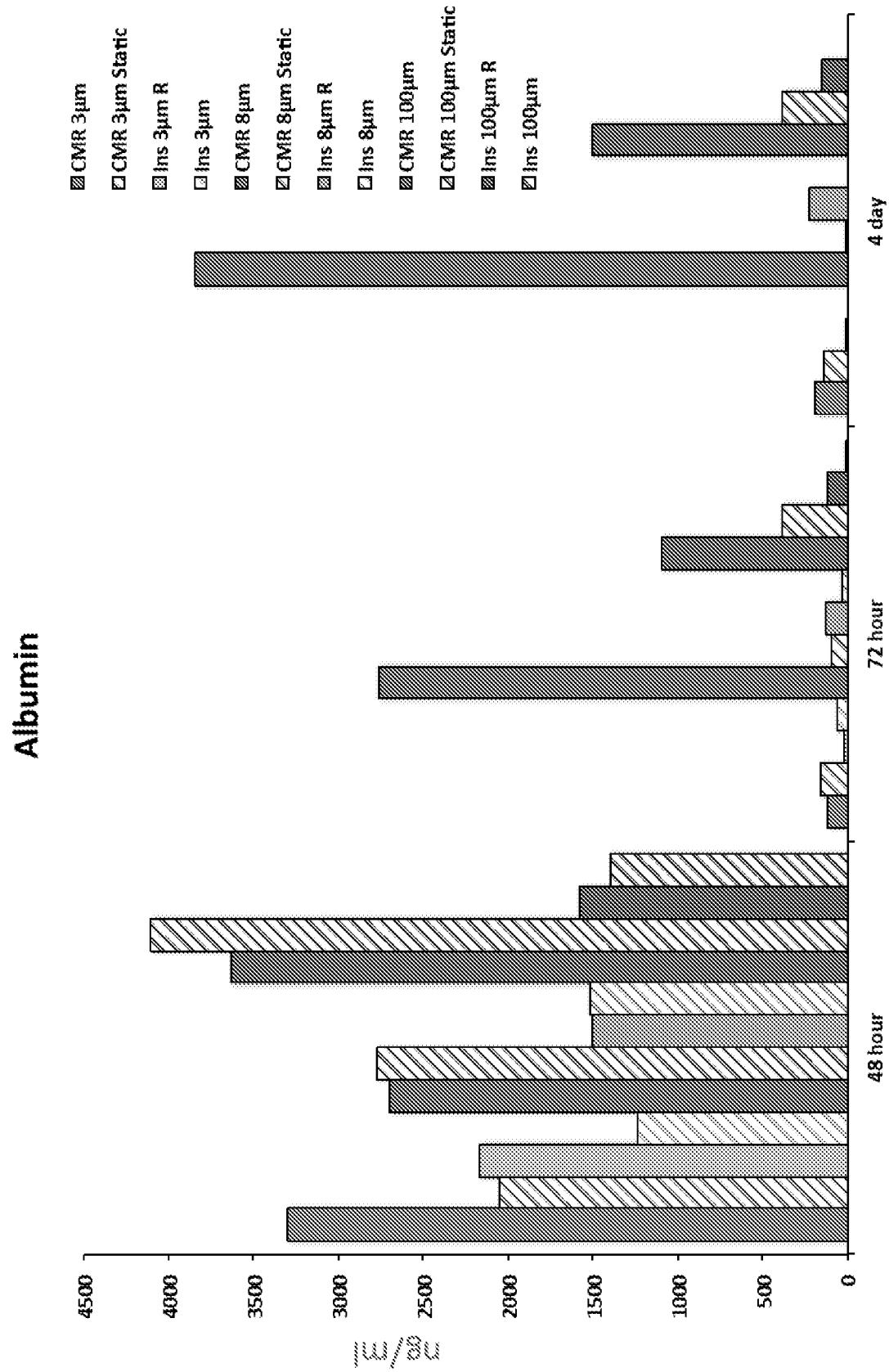

FIG. 10 is a graph illustrating that the effect of cell scaffold insert pore size on and rocking the bioreactor plate to introduce a bidirectional flow and media exchange on albumin secretion (ng/ml). Conclusion: albumin production and tissue viability is improved with bidirectional flow on inserts pore sizes between 8 μm-100 μm. 3 μm pore inserts did not improve slice function, n=1.

Figure 11:
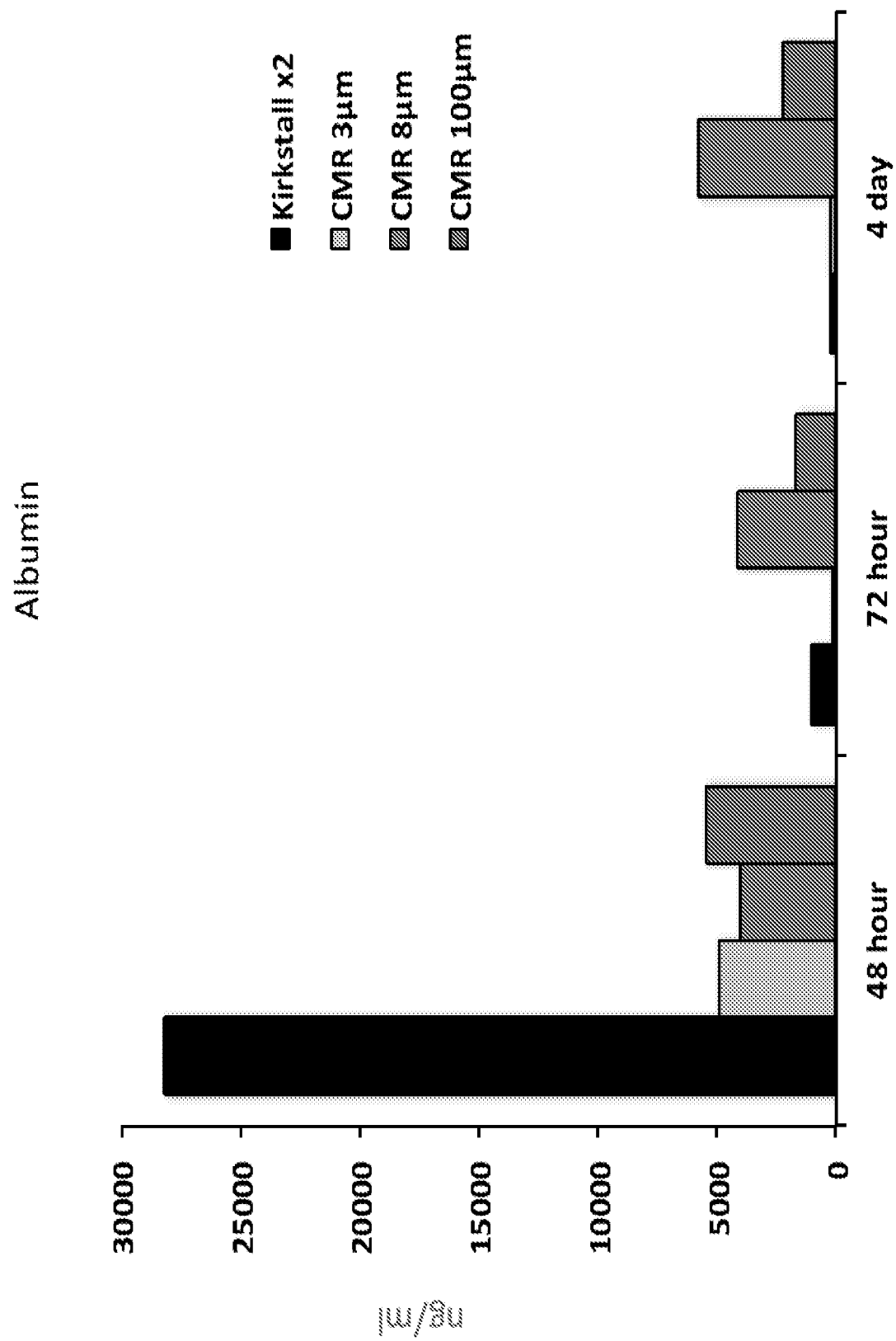

FIG. 11 is a graph comparing that the effect of unidirectional flow using a system available from Kirkstall Limited, UK, ("Kirkstall") versus bidirectional flow (rocked CMR plate, "CMR") with 3 μm, 8 μm or 100 μm inserts on albumin secretion (ng/ml). Conclusion: bidirectional flow results in albumin secretion which is stable for longer. The minimum pore size needed to improve function is required to improve albumin synthesis and secretion.

Figure 12:
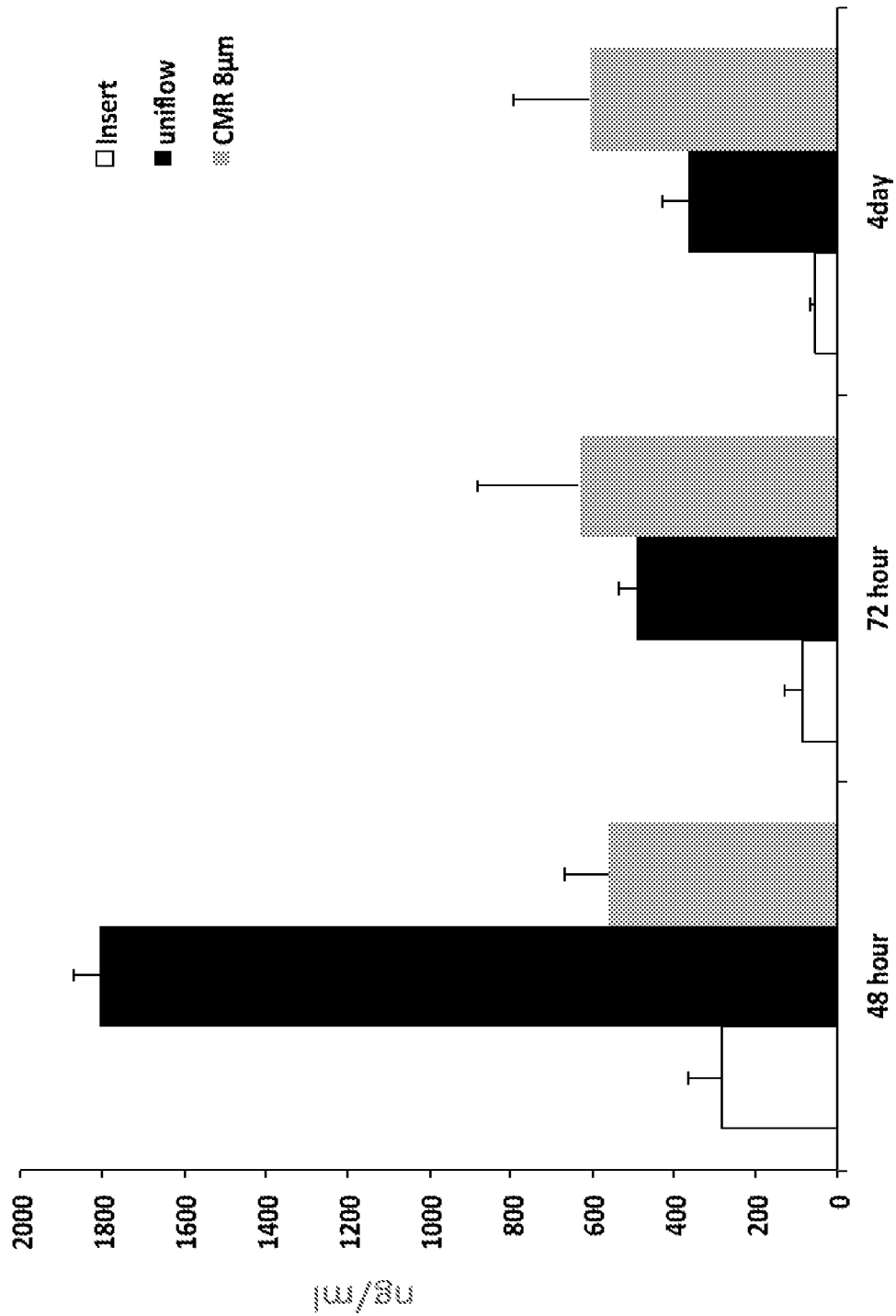

FIG. 12 is a graph comparing that the effect of unidirectional flow using a unidirectional flow system, (uniflow, black bars) versus bidirectional flow (rocked CMR plate, with 8 μm pores) on albumin secretion (ng/ml). Unidirectional flow system, (uniflow) versus CMR I and static insert data indicates that when bidirectional flow is provided, albumin secretion is stable for longer.

Figure 13:
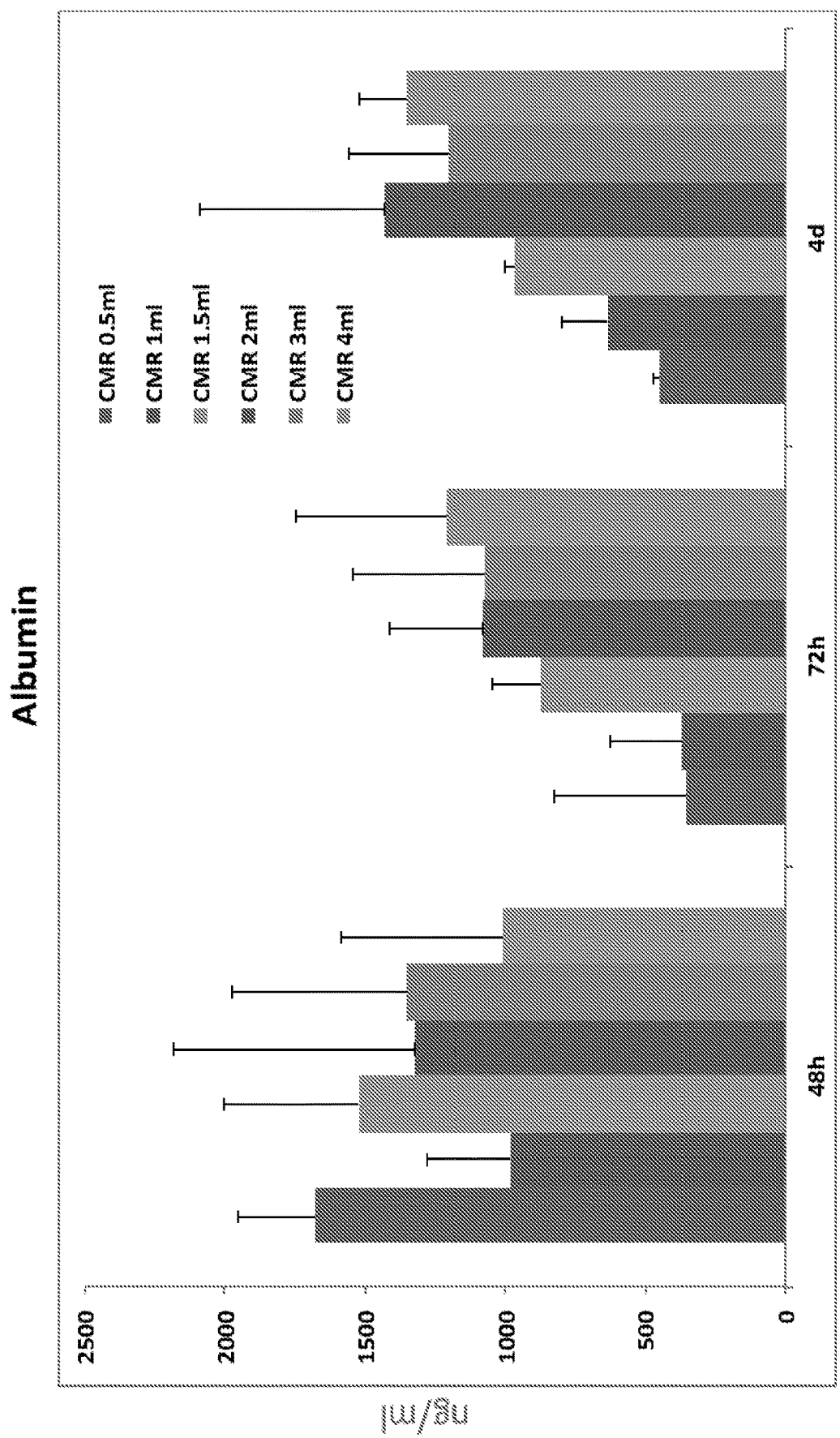

FIG. 13 is a graph showing albumin production (ng/ml) in the CMR bioreactor plate with 8 μm inserts and rocking with increasing volumes of culture media within the chamber from 0.5 ml/well (total chamber volume 1 ml) to 4 mls/well (total chamber volume 8 mls). The media volume range that improves liver function and retains albumin secretion is between about 1.5 ml-4 mls.

Figure 14:
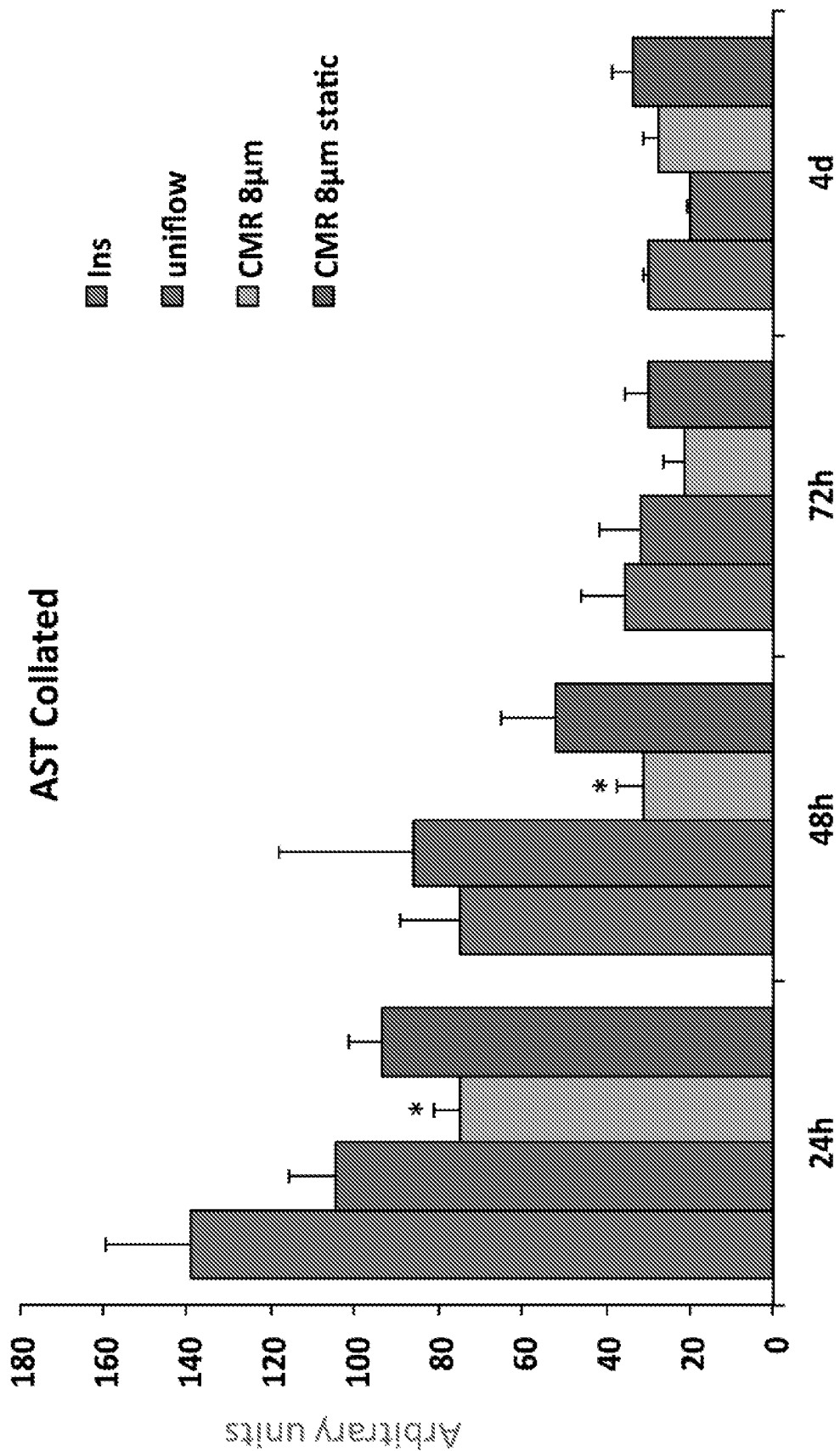

FIG. 14 is a graph illustrating that liver damage quantified by leakage of the liver enzyme aspartate aminotransferase from damaged hepatocytes (arbitrary units) is reduced in CMR cultured slices compared to static conditions or conditions provided by a unidirectional flow system, (uniflow). Rocking the CMR bioreactor plate with 8 µm inserts ("CMR 8") improves slice viability compared to static conditions ("CMR 8S") or unidirectional flow system, (uniflow), suggesting bidirectional flow is important to prevent death of the liver slice.

Figure 15:
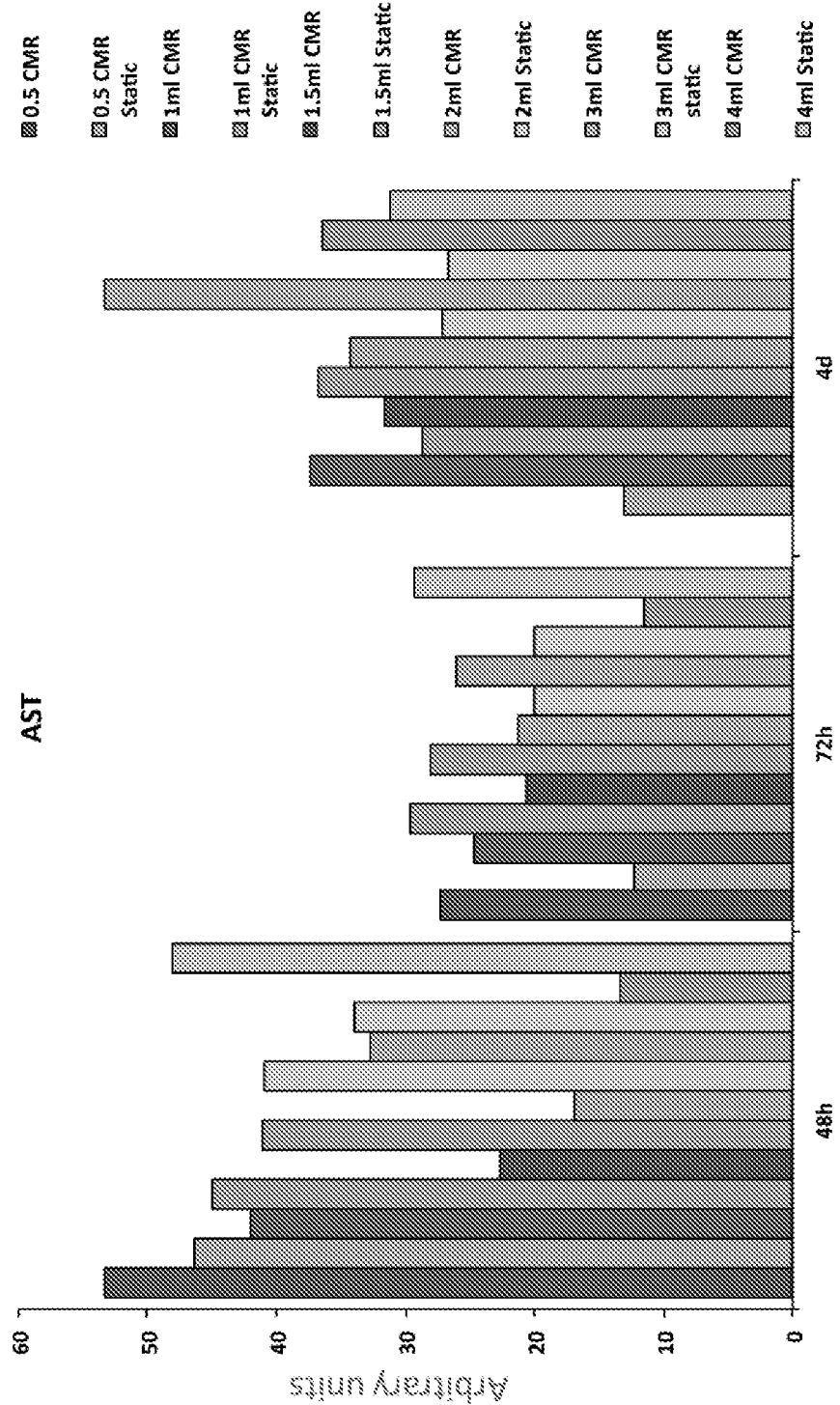

As indicated, serum transaminases are reduced using the CMR plate according to certain embodiments of the present invention (8 µm compared to static inserts (Ins 1.5) or unidirectional flow system (uniflow)). N=3. Statistics are unpaired t-test compared to static inserts;

FIG. 15 is a graph illustrating that liver damage quantified by leakage of the liver enzyme aspartate aminotransferase from damaged hepatocytes (arbitrary units) is reduced in CMR cultured slices compared to static conditions when the media volume of the CMR is between 1.5 mls-2 mls. Media volumes below 1.5 mls do not prevent tissue death. 8 µm pore inserts were used. Conclusion: Serum transaminases are reduced when the hepatocytes are cultured using CMR (1.5 mls-2 mls media), suggest less damage to the slice. The bars run left to right as labelled from top to bottom.

Figure 16:
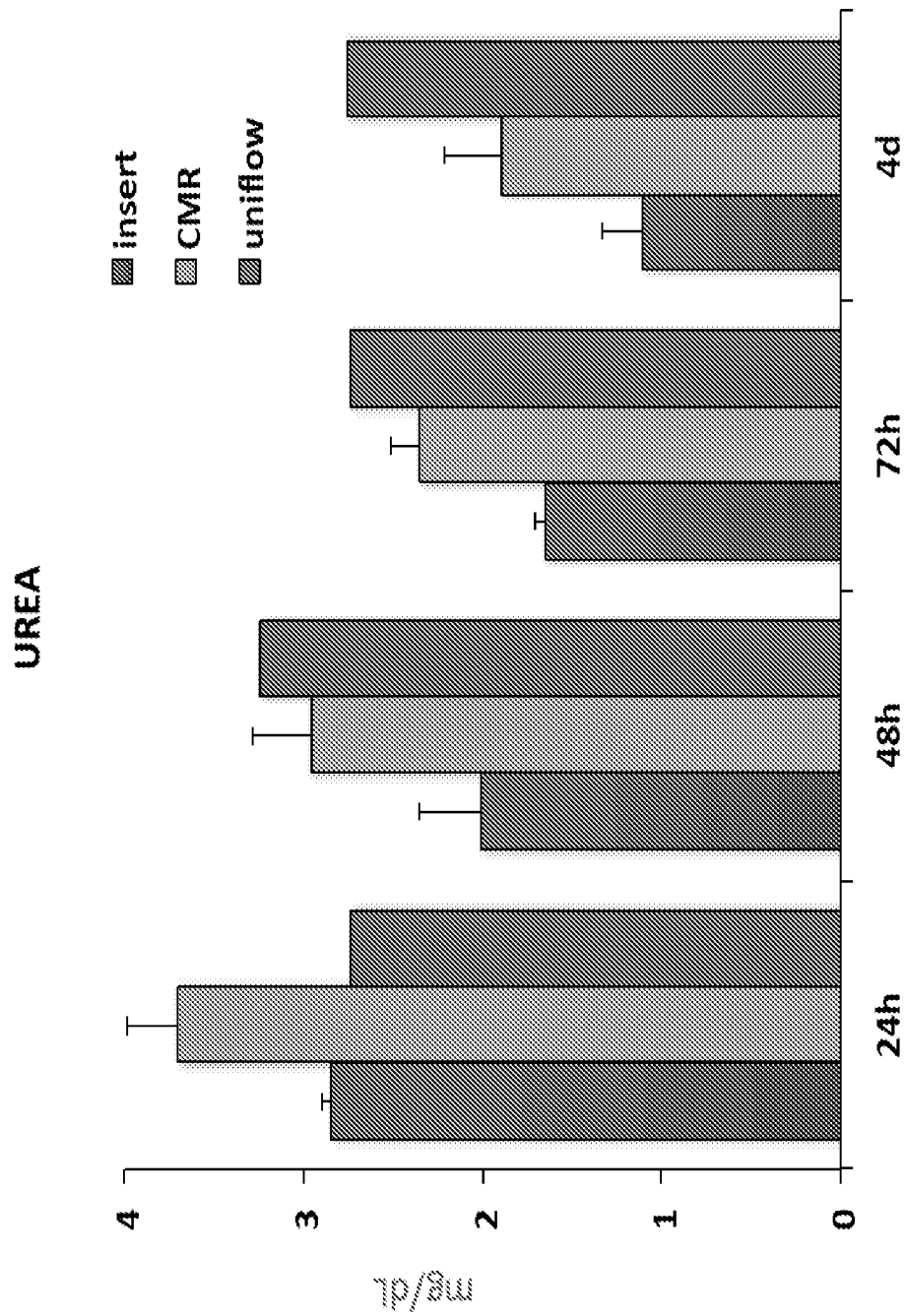

FIG. 16 is a graph illustrating urea production from liver slices cultured in static inserts (Ins 1.5), a well having pores of 8 µm of a plate according to certain embodiments of the present invention and those cultured in a unidirectional flow system (uniflow). Conclusion: Liver function is improved in CMR cultured slices compared to static conditions. UREA production (mg/dL) is increased on CMR (8 µm) compared to static inserts (Ins 1.5) or unidirectional flow system, (uniflow). n=2 (CMR and static insert) n=1 uniflow.

Figure 17:
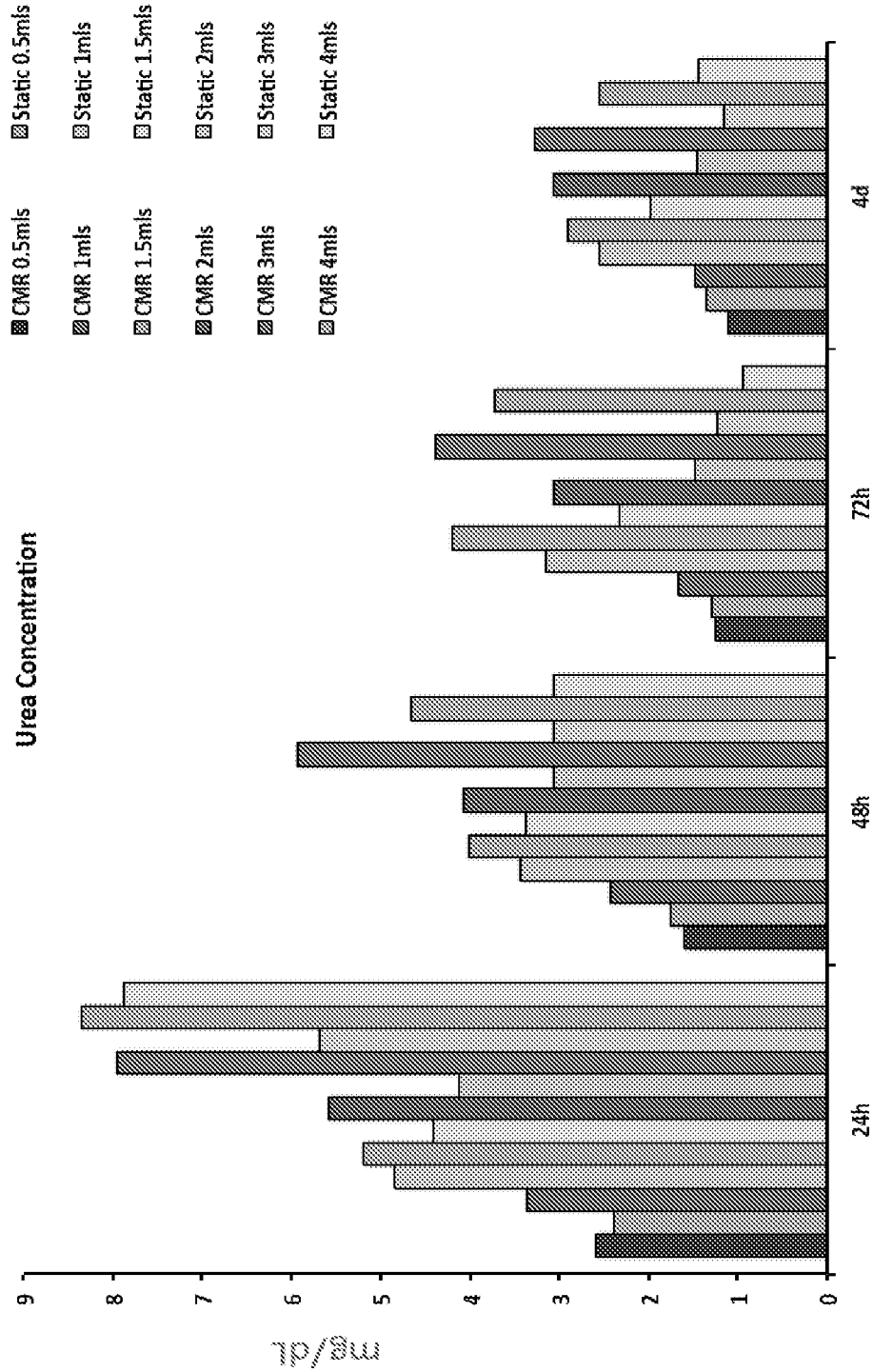
Figure 18:
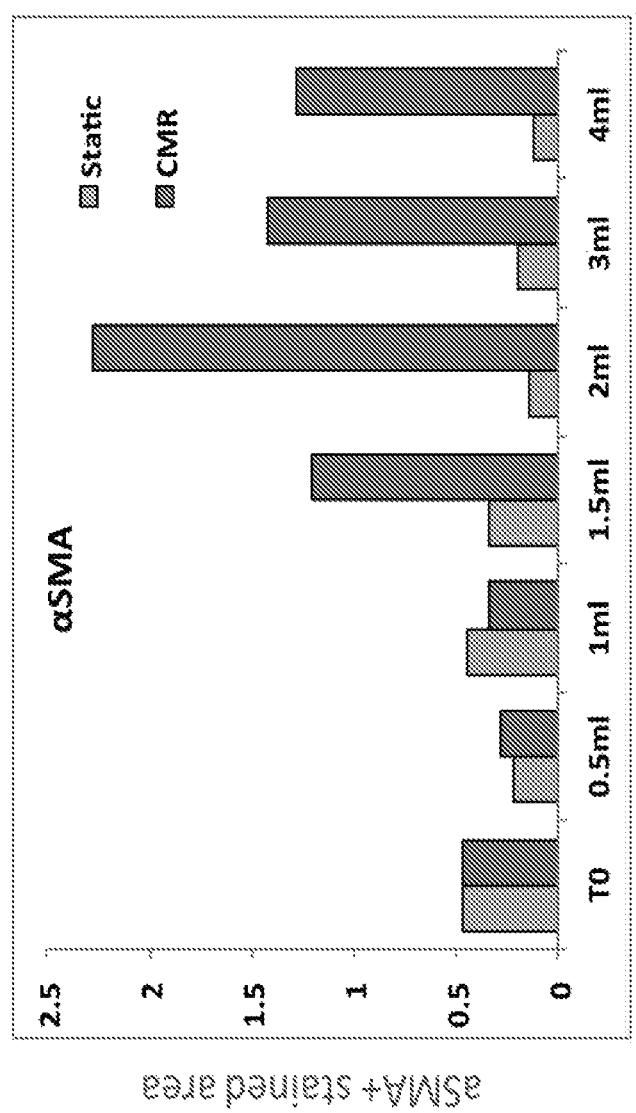

FIG. 17 is a graph illustrating urea production (mg/dL) on the CMR with wells having 8 µm pore inserts versus static inserts over a media range of 0.5 mls-4 mls. The data suggest a dynamic range of 1.5 mls-4 mls/well, n=1 and media volumes between 1.5 mls-4 mls on a rocked CMR plate preserve urea synthesis and secretion. The bars run left to right as labelled from top to bottom;

FIG. 18: is a graph illustrating the tissue area stained with a-smooth muscle actin (α-SMA) a marker of hepatic myofibroblasts in histological sections of liver slices at t-0 (post slice without culture) or cultured on the CMR (8 µm pore inserts) (CMR bars) versus static inserts (Static bars) over a media range of 0.5 mls-4 mls.

The data suggest that hepatic myofibroblasts are activating by day 4 in CMR in media volumes of 1.5 mls-4 mls, n=1.

Figure 19:
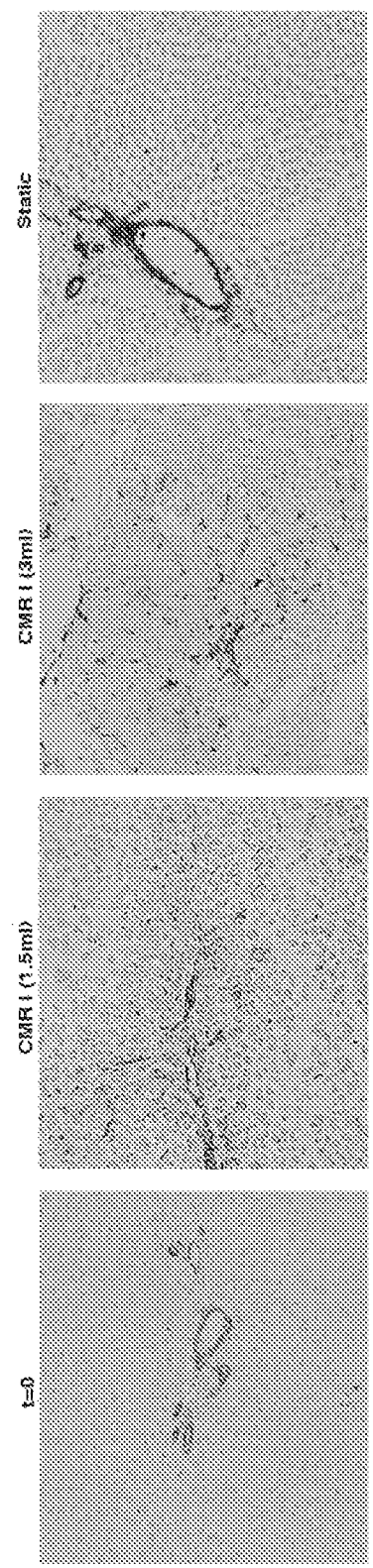

FIG. 19 illustrates representative images of histological sections of liver slices at t-0 (post slice without culture) or cultured on the CMR (8 µm pore inserts) in 1.5 mls or 3 mls of media versus static inserts and stained with α-smooth muscle actin (α-SMA) a marker of hepatic myofibroblasts. This suggests that hepatic myofibroblasts are activating by day 4 in CMR, n=1. This may be of use for modeling liver disease and fibrosis.

Figure 20:
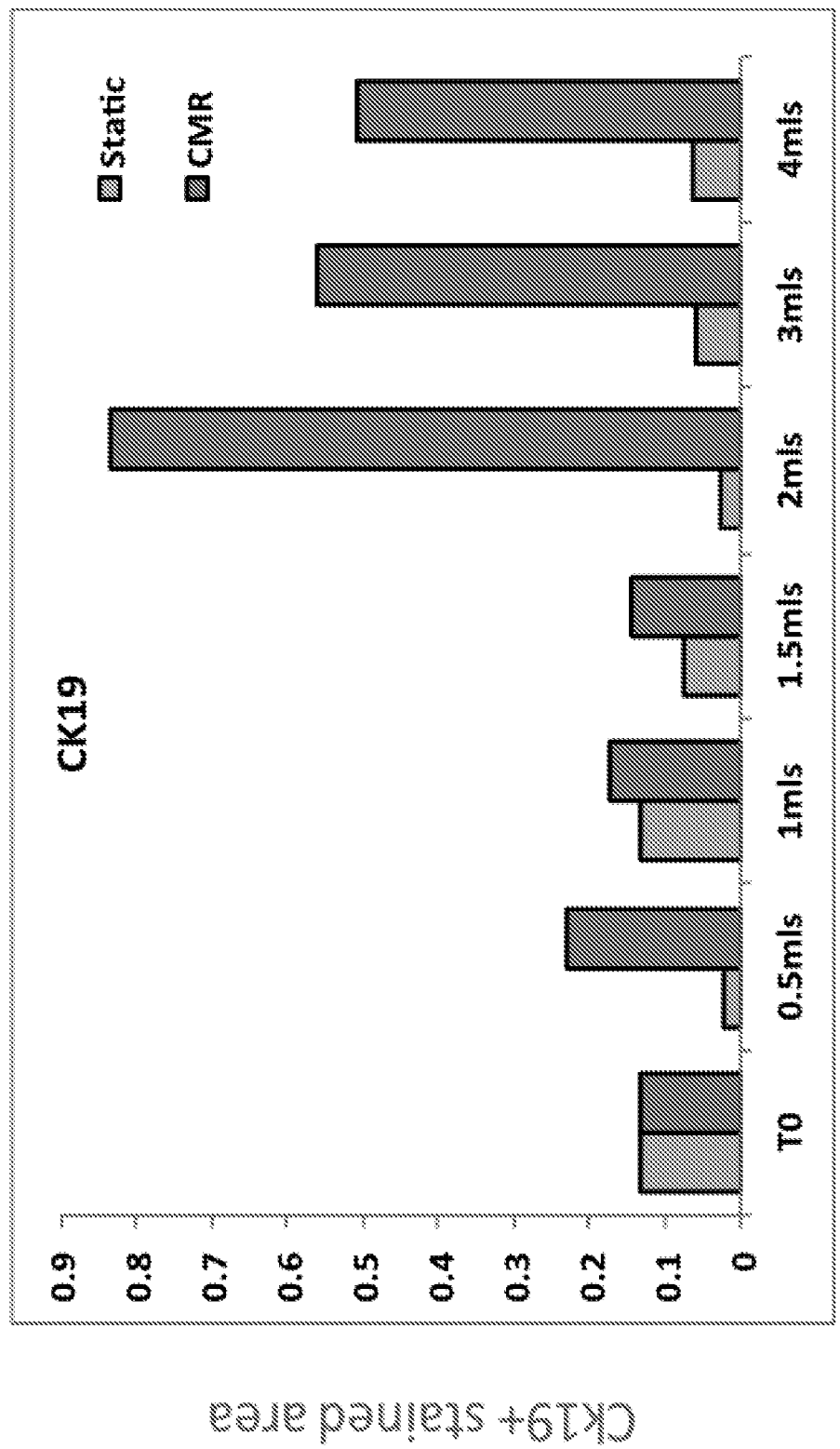

FIG. 20 is a graph illustrating the tissue area stained with cytokeratin 19 (CK19) a marker of ductular cells in histological sections of liver slices at t-0 (post slice without culture) or cultured on the CMR (8 µm pore inserts) versus static inserts over a media range of 0.5 mls-4 mls. The data suggests that a ductular expansion may occur by day 4 in >1.5 ml in the CMR, n=1. This may be of use for modeling liver disease and fibrosis.

Figure 21:
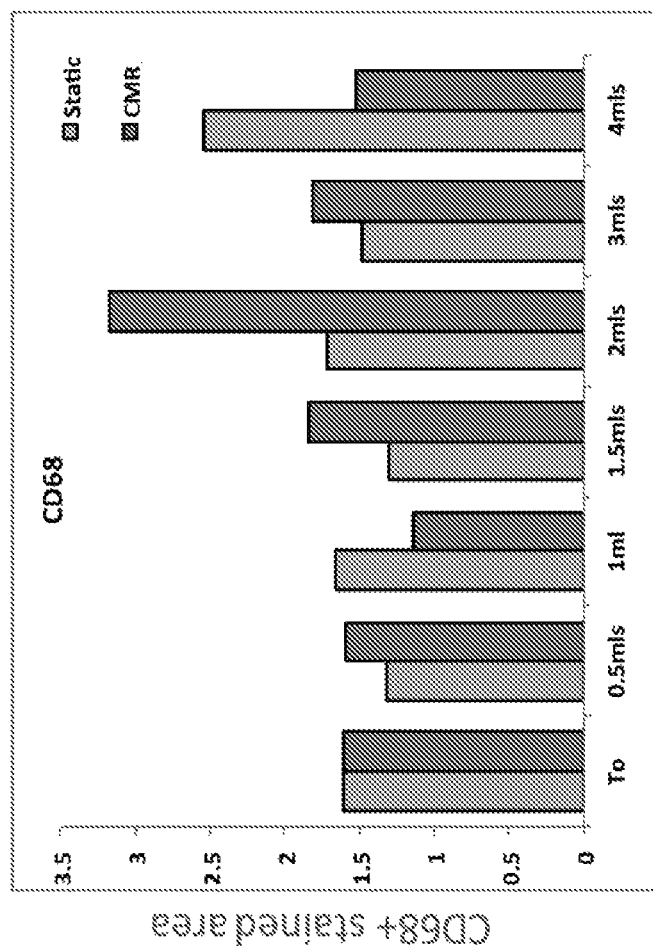

FIG. 21 is a graph comparing is a graph illustrating the tissue area stained with CD68 a marker of Kupffer cells (liver macrophages) in histological sections of liver slices at t-0 (post slice without culture) or cultured on the CMR (8 µm pore inserts) (blue bars) versus static inserts (green bars) over a media range of 0.5 mls-4 mls. The data suggests that macrophages are retained in the slices up to day 4 in CMR and Static inserts (static), n=1. This may be of use for modeling liver disease and fibrosis.

Figure 22:
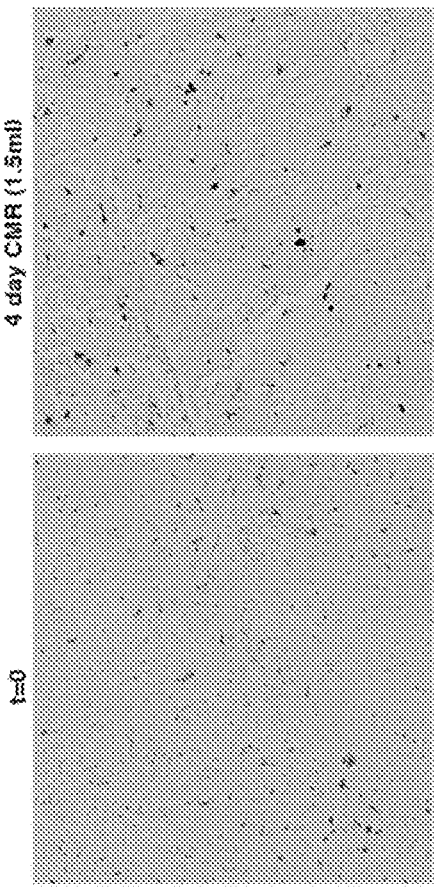

FIG. 22 shows representative images of histological sections of liver slice at t-0 (post slice without culture, left) or cultured on the CMR (8 µm pore inserts) in 1.5 mls of media (right) and stained with CD68 a marker of Kupffer cells (liver macrophages). Conclusion: macrophages are retained in the slices up to day 4 in CMR.

Figure 23:
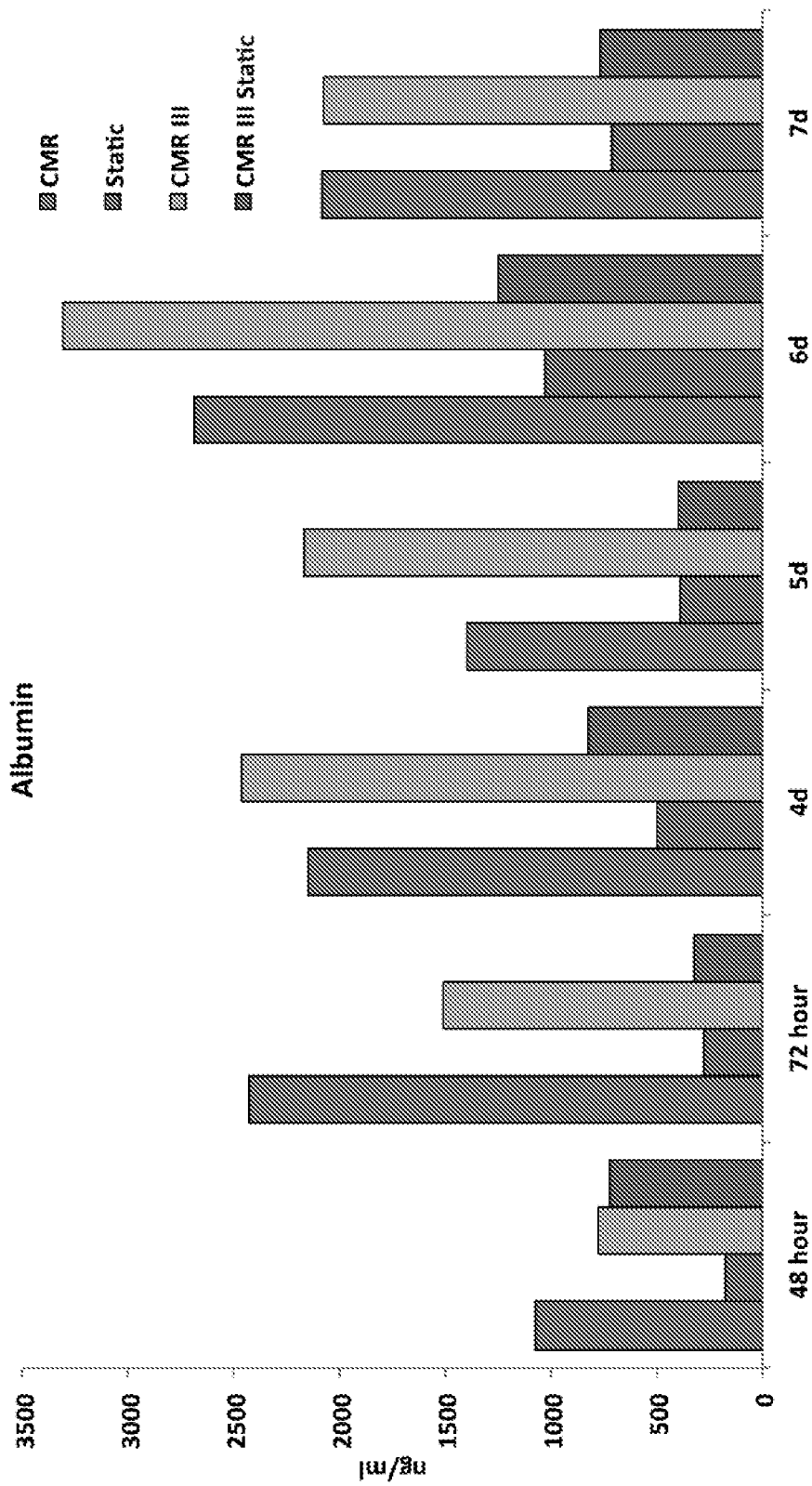

FIG. 23 is a graph illustrating the production of albumin (ng/ml) using a static cell culture plate and apparatus according to certain embodiments of the invention. Conclusion: CMR plate version comprising through holes between chambers (CMR) and an embodiment which comprises slots between chambers (CMR III) work equally well and preserves stable albumin synthesis and secretion for up to 7 days, n=1. 8 µm pore inserts was used.

Figure 24:
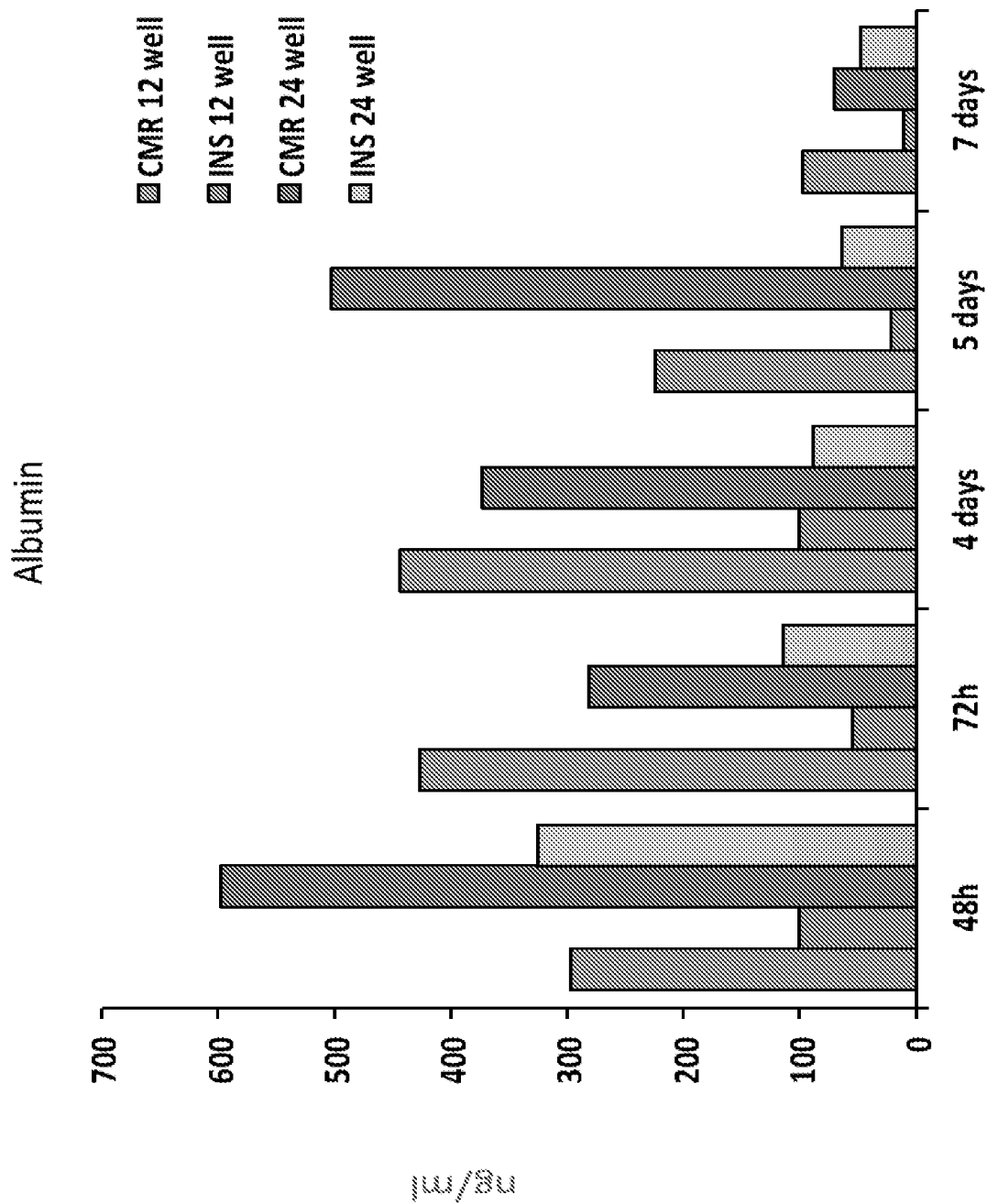

FIG. 24 is a graph comparing albumin production of 6 mm liver slices cultured in the CMR (12 well) with 8 µm inserts with CMR (24 well) 8 µm inserts. The data shows that the 24 well CMR system works as well the 12 well CMR system.

Figures 25A, 25B:
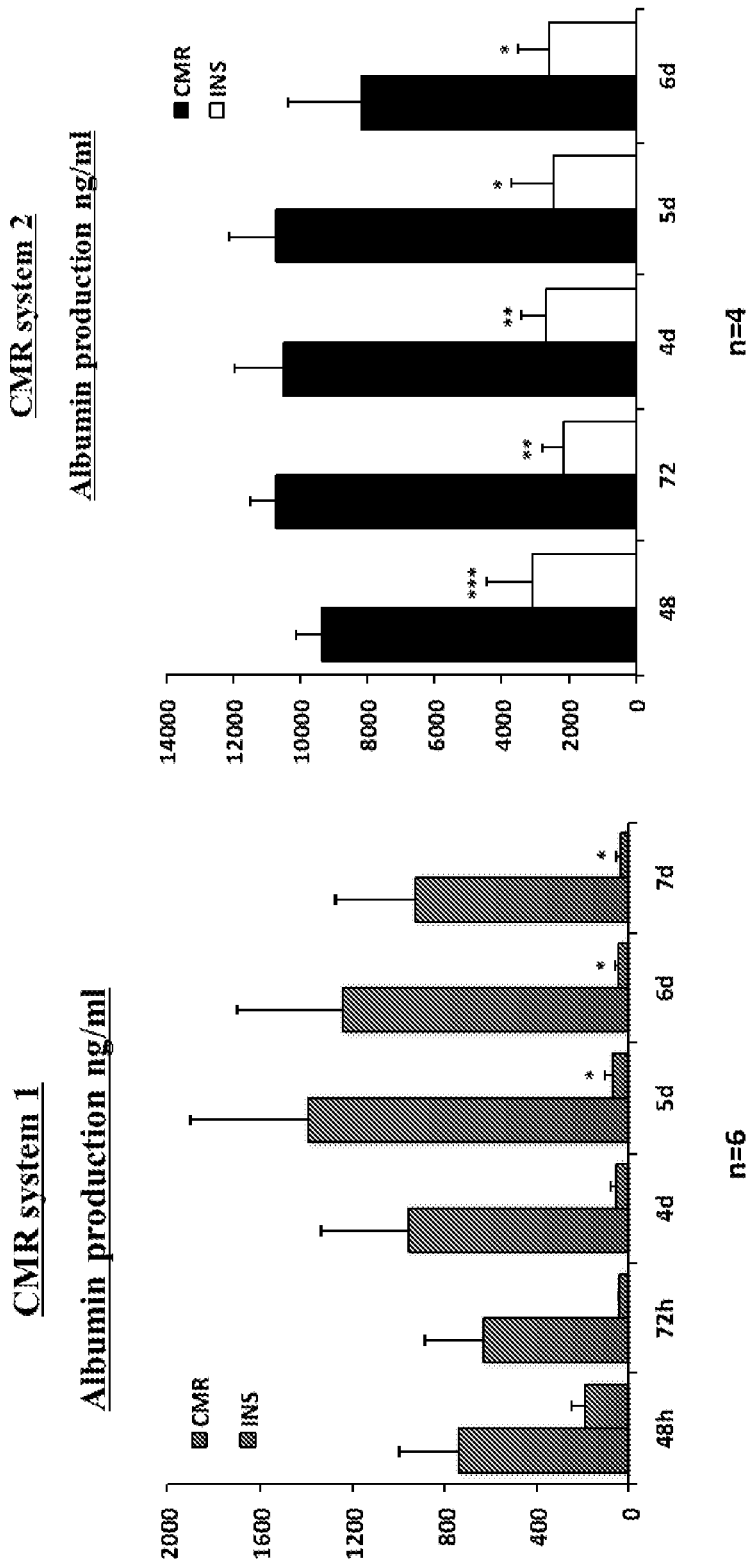

FIG. 25 is a graph showing quantification of albumin production in precision cut liver slices (PCLS) cultured on either the CMR versus static trans-well insert cultures (25A) or CMR2 versus static trans-well insert cultures (25B) for up to 7 days with daily media changes. Similar to CMR, the CMR2 bioreactor maintained albumin production, compared to static trans-well insert cultured slices. The bars run left to right as labelled from top to bottom.

Figures 26A, 26B:
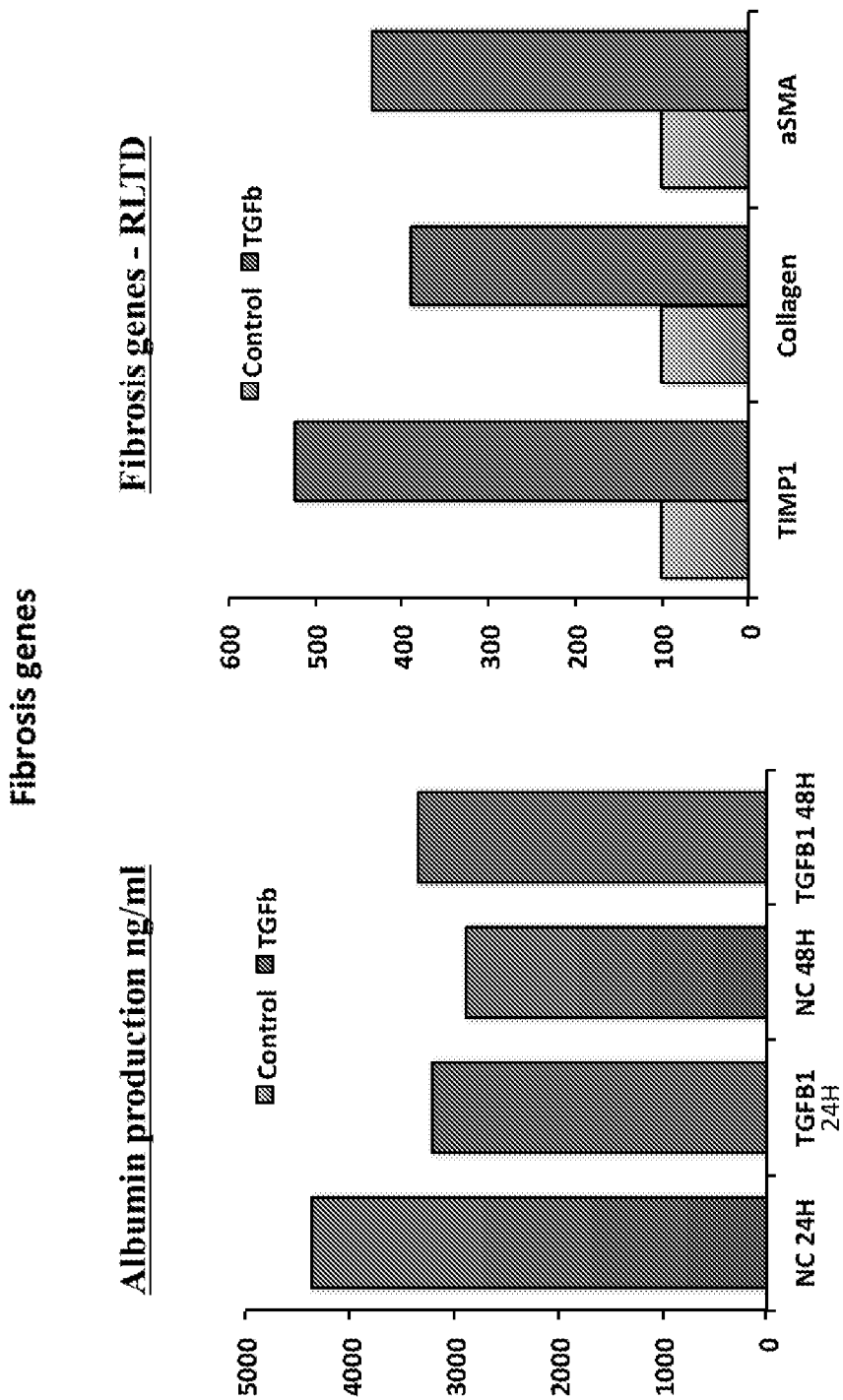

FIG. 26 is a graph showing albumin production by PCLS cultured on CMR2 and stimulated +/−3 ng/ml transforming growth factor beta 1 (TGFb1) for 48 h after a 24 h rest period (FIG. 26A). FIG. 26B shows that treatment of PCLS with 3 ng/ml TGFb1 for 48 h induced expression of the fibrosis genes collagen I, alpha-smooth muscle actin (aSMA) and tissue inhibitor of metalloprotease 1 (TIMP1) compared to control (untreated). The bars run left to right as labelled from top to bottom.

Figures 27, 28:
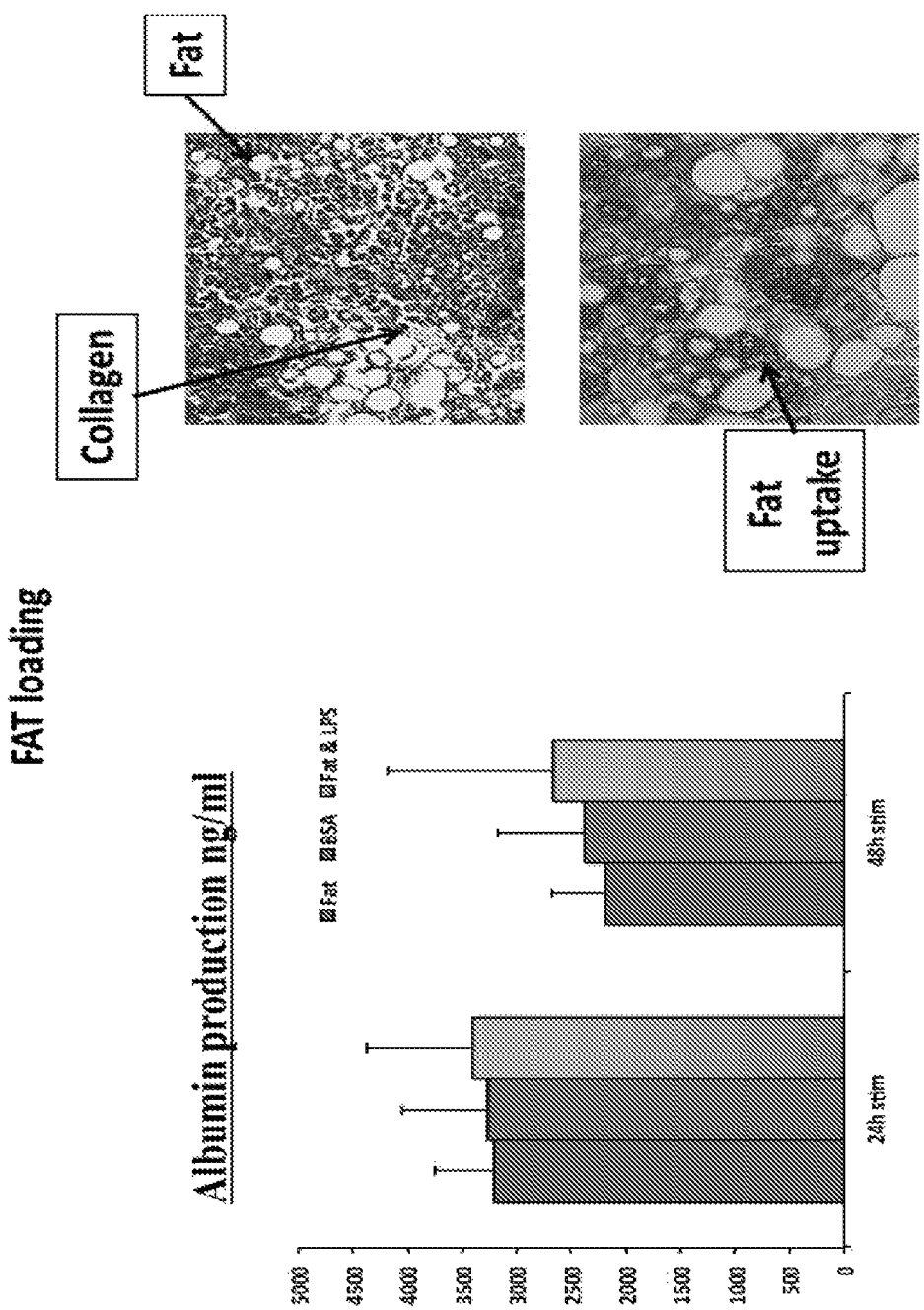

FIG. 27 shows albumin production by PCLS cultured on CMR2 and stimulated +/− fat, fat+Lipopolysaccharide (LPS) or Bovine Serum Albumin (BSA, vehicle) for 48 h after a 24 h rest period. Treatment with FAT or LPS did not affect albumin production.

FIG. 28 is images show that the fat treatment induces fat accumulation and deposition of collagen in the PCLS.

FIGS. 29A, 29B and 29C are perspective views of an apparatus according to certain embodiments of the present invention (referred to herein as CMR2).

Figure 29:
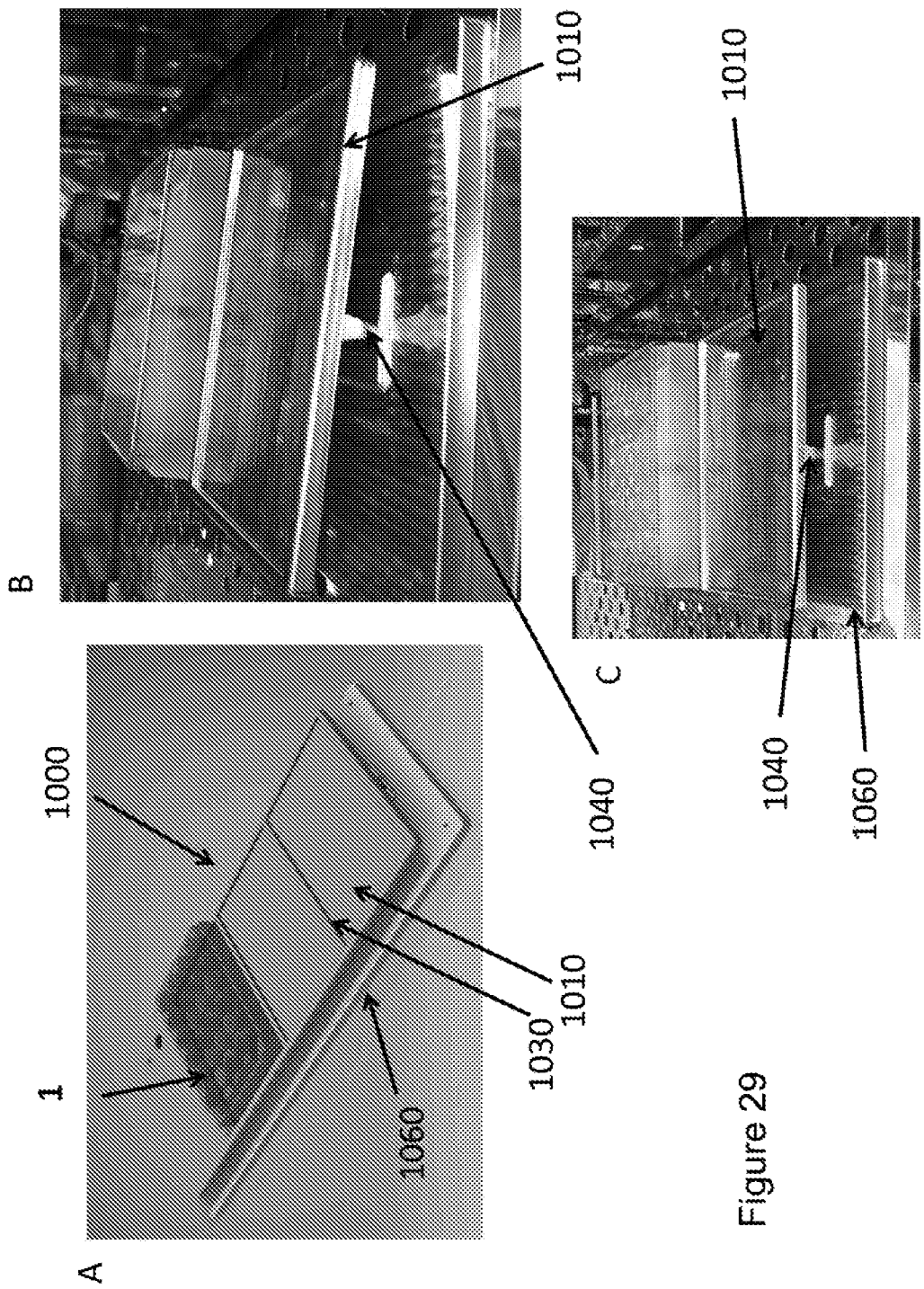

FIG. 30A and FIG. 30B depict various components of the apparatus of FIG. 29.

Figure 31:
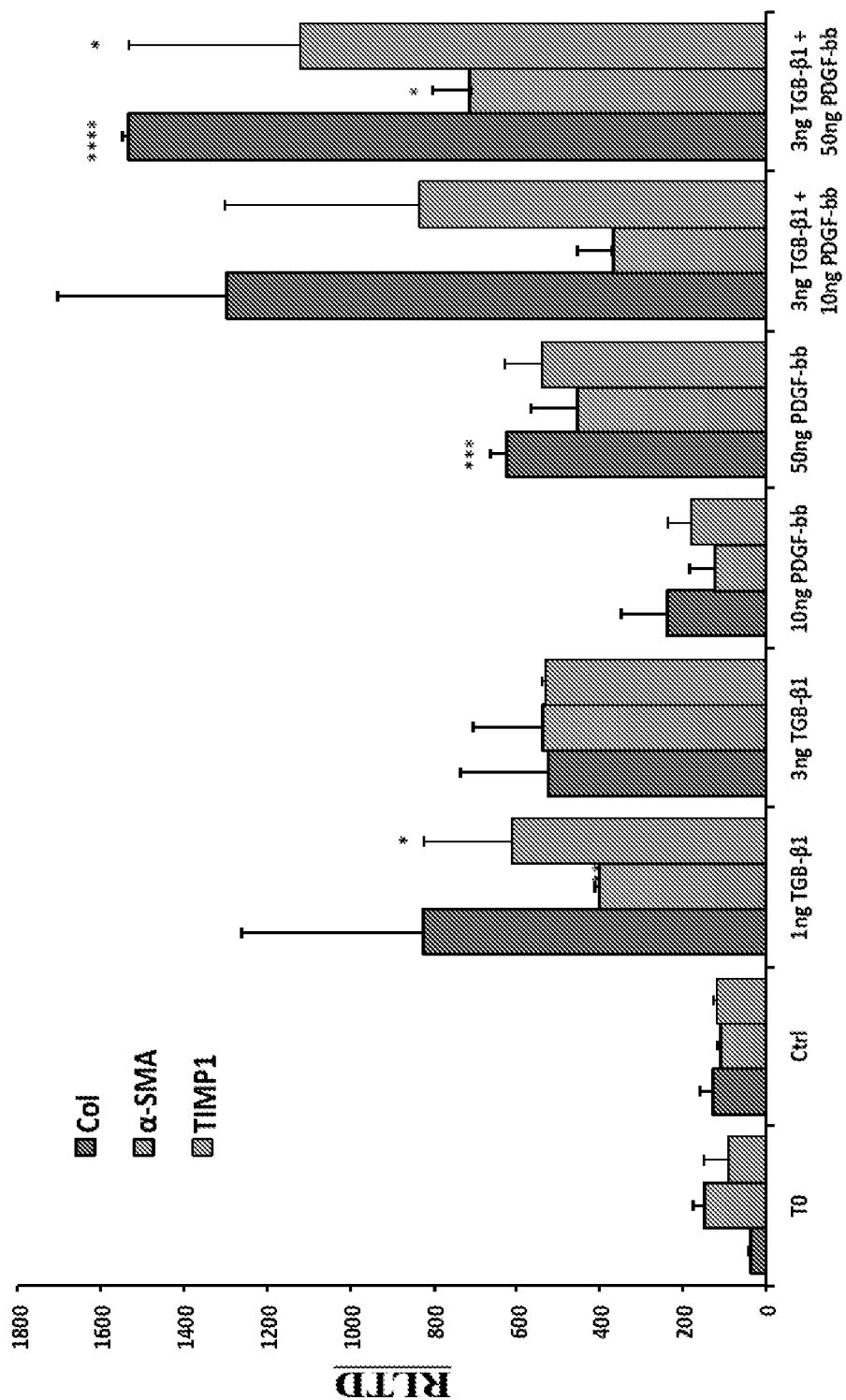

FIG. 31 is a graph showing expression of the fibrotic genes pro-collagen 1, alpha-smooth muscle actin (aSMA) and Tissue inhibitor of metalloproteinase 1 (TIMP1) in precision cut liver slices (PCLS) cultured on CMR2 and stimulated +/− transforming growth factor beta (TGFb) and +/− platelet derived growth factor b (PDGF-bb) for 72 h after a 24 h rest period. Treatment with both stimuli induce expression of fibrosis genes.

Figure 32:
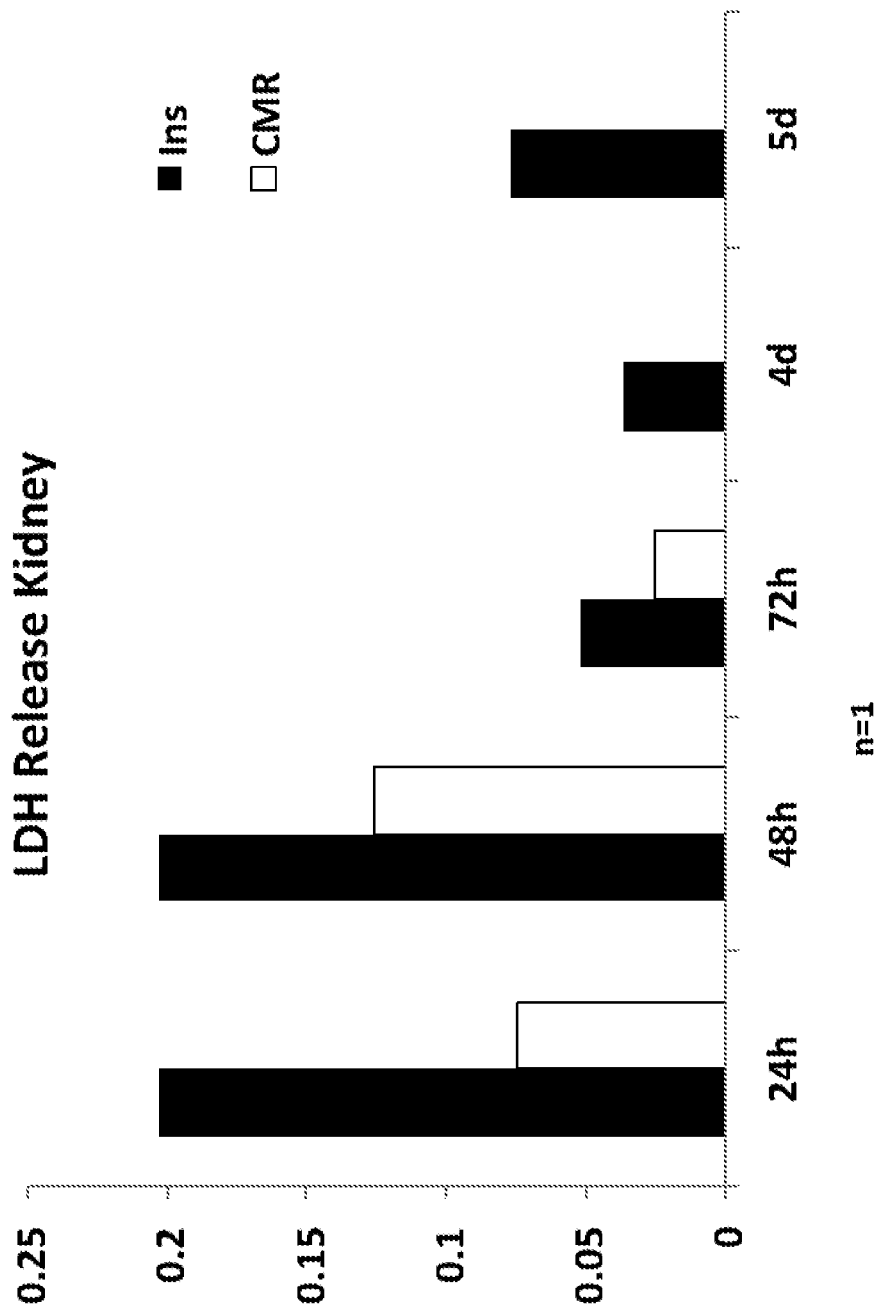

FIG. 32 is a graph showing quantification of lactate dehydrogenase (LOH) release in precision cut kidney slices (PCKS) cultured on either the CMR versus static trans-well insert cultures for up to 5 days with daily media changes. PCKS damage as determined by LOH release is reduced on CMR cultured slices compared to static TRANSWELL® permeable support insert cultured slices.

DEFINITIONS

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. As employed throughout the disclosure, the following terms, unless otherwise indicated, shall be understood to have the following meanings:

It will be appreciated that the terms "chamber" and "well" as used herein are interchangeable and are exemplary and non-limiting. The mention of one term does not exclude substitution of the other terms in the described embodiment. As used herein, a chamber is an orifice in a holder body which typically comprises a flat planar base and an upper opening. The chamber may be cylindrical in shape and have one or more side walls. Further details of exemplary chambers are provided herein.

As used herein, the term "cell culture" or "culture" refers to the maintenance, growth, differentiation and/or continued viability of cells in an artificial, in vitro environment. The cells may be comprised in a tissue or portion thereof e.g. a tissue or organ slice. The cell culture may be a two dimensional cell culture or a three dimensional cell culture. In one embodiment the organ slice may be for example a liver slice, a kidney slice or a lung slice.

An "organ slice" or "tissue slice" is an in vitro model which represents the multi-cellular, structural and functional features of in vivo tissue. Tissue slices may provide a model for characterising mechanisms of drug-induced injury and for identifying biomarkers of organ injury, which can be a significant clinical issue.

Certain embodiments of the present invention may have particular utility culturing tissue slices comprising different cell types for extended periods of time and therefore may provide an in vitro model of an in vivo tissue or organ environment. Regional differences and changes in morphology can be readily evaluated by histology and special stains, similar to tissue obtained from in vivo studies.

The tissue slice may be of any suitable size. In certain embodiments, the tissue slice is between about 4 mm and 10 mm in diameter. Aptly, the tissue slice may be about 6 mm in diameter. Aptly, the tissue slice is a liver or a kidney slice having a thickness of 200-300 μm and cores of between about 4-8 mm diameters. Aptly, the tissue slice is a lung slice having a thickness of 200-500 μm and cores between about 4-8 mm in diameter.

In certain embodiments, liver tissue slices can be a beneficial model as they retain liver structure, contain all the cell types found in vivo, have good in vitro/in vivo correlation of xenobiotic metabolism, and maintain zone-specific cytochrome activity (allowing for cellular and zonal toxicity) and mechanisms of toxicity.

A three-dimensional cell or tissue culture may be differentiated from a two-dimensional cell or tissue culture which is typically provided by a flat layer of cells supported by a base surface of a chamber or well. Three dimensional cell cultures are aptly cellular networks in which cells are round and organised in three dimensions, an environment and cell morphology that are more similar to that found in viva A 3-D cell culture may be provided by a scaffold.

As used herein, the terms "cell scaffold" and "tissue scaffold" refer to an artificial three-dimensional porous solid structure. These scaffolds serve to mimic the actual in vivo microenvironment where cells interact and behave according to the mechanical cues obtained from the surrounding 3D environment. A variety of cell scaffold materials are available. Suitable materials include for example, polymer microfibers or nanofibers e.g. electrospun nanofibers. Suitable polymers include e.g. poly(L-lactide) (PLLA) and poly(D,L-lactide) (PDLLA). The scaffold can be made using conventional techniques such as for example silicon processing technology, micromachining, injection moulding and rapid additive manufacturing techniques.

As used herein, the phrases "medium", "cell culture medium", "tissue culture medium," "culture medium" (plural "media" in each case) and "medium formulation" refer to a nutritive solution suitable for cultivating cells or tissues e.g. mammalian cells. These phrases can be used interchangeably. Cell culture media formulations are well known in the art. Typically, a cell culture medium is composed of a number of ingredients and these ingredients can vary from medium to medium. Cell culture media are typically comprised of buffers, salts, carbohydrates, amino acids, vitamins, and trace essential elements. The selection of cell culture media will be dependent on e.g. cell type and other factors.

The cell culture medium may or may not contain serum, peptone, and/or proteins. Various tissue culture media, including serum-free and defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Williams E Medium, Leibovitz's L-15 Medium, and serum-free media such as EX-CELL™ 300 Series (JRH Biosciences, Lenexa, Kans.), among others. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

Aptly, the methods of certain embodiments may be for culturing cells from any source including eukaryotic cells and prokaryotic cells, e.g. plant cells, mammalian cells, yeast cells, fungal cells and/or bacterial cells. Aptly, the cell culture comprises mammalian cells selected from epithelial cells, tumour cells, hepatocytes, fibroblast cells, stem cells, myocardiocytes, kidney cells, lung cells, neuronal cells, adipocytes, intestinal cells, skin cells, immune cells, either alone or in combination.

In certain embodiments, the mammalian cells are selected from tumour cells, stem cells and primary epithelial cells (e.g., keratinocytes, cervical epithelial cells, bronchial epithelial cells, tracheal epithelial cells, kidney epithelial cells and retinal epithelial cells).

Aptly, the mammalian cells may be human. The mammalian cells may be sourced from an individual e.g. a patient suffering from a disorder. In certain embodiments, the cells (e.g. in an organ slice) may be isolated from a patient suffering from, or at risk of, a fibrotic disease. The fibrotic disease may be for example a fibrotic disease affecting the liver, the kidneys or the lungs. The patient may be suffering from a disorder which may progress to a fibrotic disease.

In certain embodiments, the cells may be sourced from established cells lines. In certain embodiments, the cells may be genetically modified. In certain embodiments, the cells are from established cell lines such as for example, 293 embryonic kidney cells, HeLa cervical epithelial cells and PER-C6 retinal cells, MDBK (NBL-1) cells, CRFK cells, MDCK cells, CHO cells, Chang cells, Detroit 562 cells, HeLa 229 cells, HeLa S3 cells, Huh7, Hep3b, A549, BEAS-2B, Calu-3, Hep-2 cells, KB cells, LS 180 cells, LS 174T cells, NCI-H-548 cells, RPMI 2650 cells, SW-13 cells, T24 cells, WI-28 VA13, 2RA cells, WISH cells, BS-C-I cells, LLC-MK$_2$cells, Clone M-3 cells, 1-10 cells, RAG cells, TCMK-1 cells, Y-1 cells, LLC-PK$_1$ cells, PK(15) cells, GH.sub.1 cells, GH$_3$cells, L2 cells, LLC-RC 256 cells, MH$_1$C$_1$ cells, XC cells, MDOK cells, VSW cells, and TH-1, B1 cells, or derivatives thereof), fibroblast cells from any tissue or organ (including but not limited to heart, liver, kidney, colon, intestine, oesophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cells lines (e.g., CHO cells, TRG-2 cells, IMR-33 cells, Don cells, GHK-21 cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C.sub.3H/IOTI/2 cells, HSDM$_1$C$_3$cells, KLN$_2$O$_5$cells, McCoy cells, Mouse L cells, Strain 2071 (Mouse L) cells, L-M strain (Mouse L) cells, NCTC clones 2472 and 2555, SCC-PSA1 cells, Swiss/3T3 cells, Indian muntjac cells, SIRC cells, C$_{11}$ cells, and Jensen cells, or derivatives thereof.

In certain embodiments of the present invention, the apparatus and/or method may comprise the use and/or culture of tissues or portions thereof. The tissue may be for example an organ or a portion thereof. In one embodiment the tissue portion is a slice of an organ. Aptly, the organ may be for example, a heart, a kidney, a liver, a lung, a pancreas, a stomach, a brain. In certain embodiments, the tissues may be for example, skeletal tissue, muscle tissue, connective tissue, nervous tissue, epithelial tissue and/or mineralised tissue. In certain embodiments, the tissue portion is a liver slice or a kidney slice. Aptly, the tissue slice may further comprise multiple cell types including for example immune cells. Aptly the tissue is a human organ and the tissue portion a slice or section thereof.

In certain embodiments of the present invention, there is provided a method for testing efficacy of a candidate therapeutic molecule. A "candidate therapeutic molecule" and "candidate molecule" may act as a modulator of target molecule concentration or target molecule function in a system. A "modulator" may agonize (i.e., up-regulates) or antagonize (i.e., down-regulates) a target molecule concentration partially or completely in a system by affecting such cellular functions as DNA replication and/or DNA processing (e.g., DNA methylation or DNA repair), RNA transcription and/or RNA processing (e.g., removal of intronic sequences and/or translocation of spliced mRNA from the nucleus), polypeptide production (e.g., translation of the polypeptide from mRNA), and/or polypeptide post-translational modification (e.g., glycosylation, phosphorylation, and proteolysis of pro-polypeptides). A modulator may also agonize or antagonize a biological function of a target molecule partially or completely, where the function may include adopting a certain structural conformation, interacting with one or more binding partners, ligand binding, catalysis (e.g., phosphorylation, dephosphorylation, hydrolysis, methylation, and isomerization), and an effect upon a cellular event.

In one embodiment, the candidate molecule may be an anti-fibrotic compound as described herein.

Figure 1:
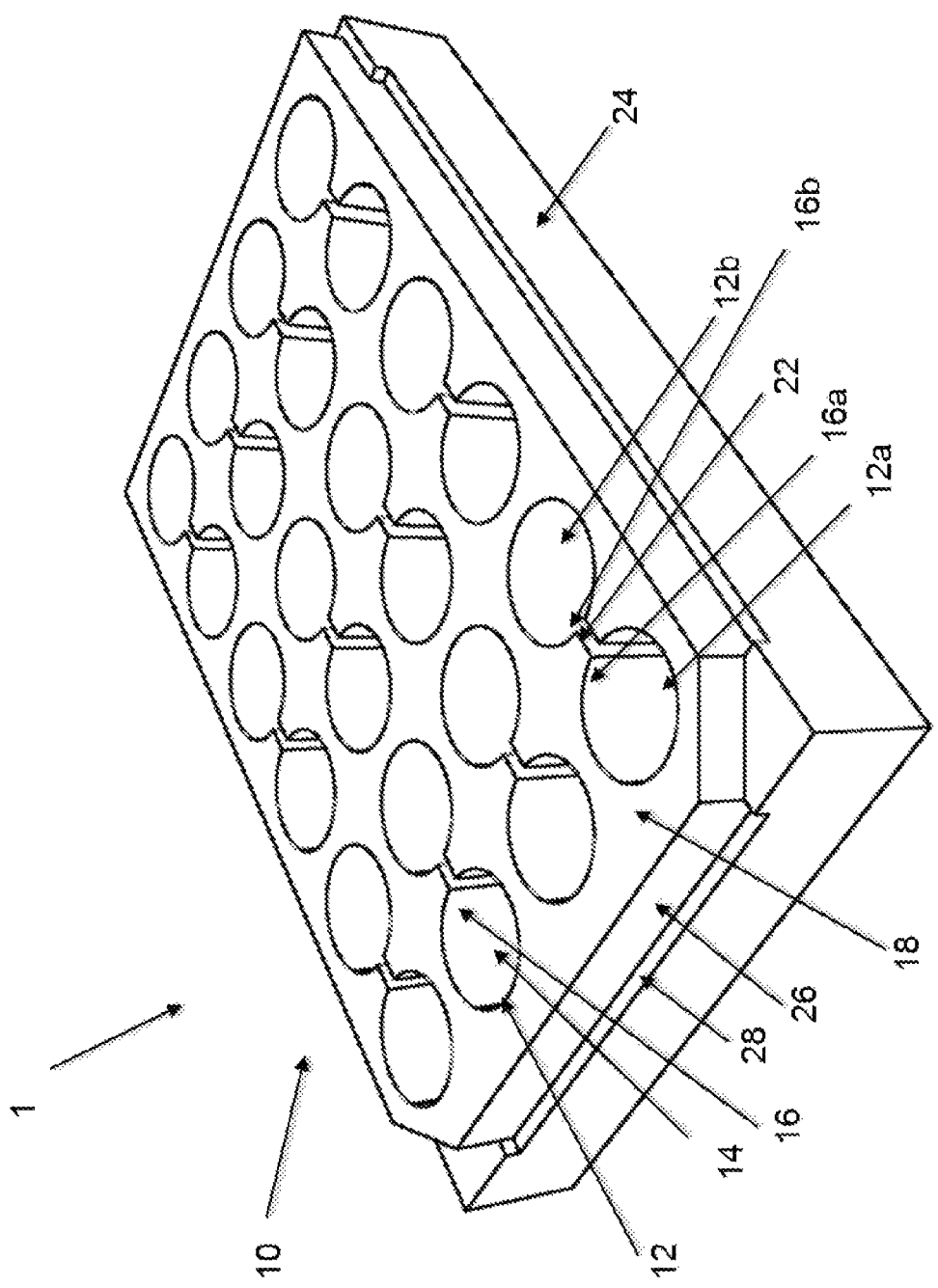
FIG. 1 illustrates a multi-well plate apparatus according to certain embodiments of the present invention.

Turning now to the Figures, certain embodiments of the apparatus according to the present invention are illustrated in FIG. 1 for example.

As shown in FIG. 1, an apparatus 1 according to certain embodiments is illustrated. The apparatus 1 is aptly a multi-well plate apparatus as detailed herein. The multi-well plate 1 comprises a holder body 10 which includes a plurality of chambers 12. The holder body is rectangular and has a lower planar surface (not shown).

In one embodiment, the apparatus is a multi-well plate. Aptly, the apparatus comprises a footprint defined by the standards of the Society for Biomolecular Sciences (e.g. Standards ANSI SLAS-1 to 4). The multi-well plate can be manufactured using known techniques including for example, rapid prototype manufacturing, moulding or the like.

The chambers may also be referred to as "wells". In the illustrated embodiment, each chamber is cylindrical. Other shapes of chamber e.g. cuboidal, are envisaged and within the scope of certain embodiments of the invention. The chambers may be arranged to receive and/or remove cell culture media. In addition, the chambers may be configured to receive and/or support an insert element, as described in more detail below.

Figure 2:
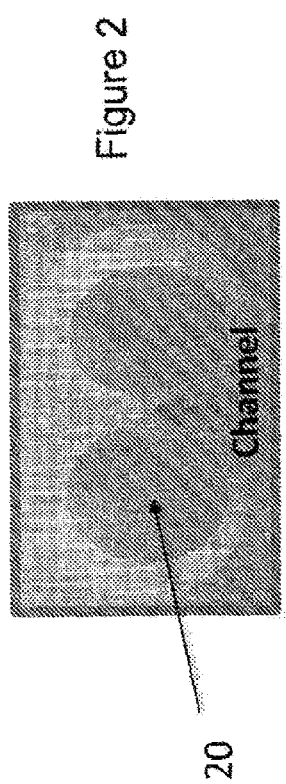
FIG. 2 is a top view of adjacent chamber of a multi-well plate apparatus according to certain embodiments of the present invention.

Each chamber 12 comprises a lower planar base 20 as shown in FIG. 2. The lower planar base in certain embodiments may alternatively be defined by a base (not shown) of the holder body. Each chamber also comprises an upper opening 14 extending through a top surface 18 of the holder body. Aptly, the upper opening is sized to enable cell culture media to be added to the chamber and/or removed therefrom. Thus, cell/tissue seeding, agent addition, sample removal, media addition and removal can be carried out via the opening of the chamber. Addition of components may be via pipette or robotics for example.

In certain embodiments, each chamber has a depth of between about 15 mm and 20 mm e.g. 15, 16, 17, 18, 19 or 20 mm. Other depths may be useful in certain embodiments.

The chamber 12 also comprises a side wall 16 extending between the lower surface and the upper opening. The wall element may not only define portions of the walls but also act to separate at least a portion of a chamber from at least a portion of an adjacent chamber.

Depending on the application of the apparatus, the base and side walls of each chamber may be formed from a transparent, translucent or opaque material. Suitable materials include for example ZEONEX™ cyclin olefin polymer (COP), ZEONOR® cyclin olefin polymer (COP), polystyrene, polycarbonate, polyethylene, polypropylene, PMMA, cellulose acetate and glass.

The chambers may be provided in any quantity and in any arrays. Aptly, the chambers are uniformly arranged in the holder body i.e. the chambers are arranged in rows and columns. The apparatus may be for example a 12-well plate, a 24-well plate, a 48 well plate or a 96-well plate. The holder body may be formed with any dimensions including for example standard dimensions for use with robotic laboratory equipment.

As shown in FIG. 1, a pair of adjacent chambers 12*a* and 12*b* are fluidly connected by a through passageway 22. The through passageway 22 provides a fluid communication pathway between the interior of a first chamber 12*a* and the interior of a second chamber 12*b*. The fluid communication pathway is aptly a through passageway and may be for example a through slit, as shown in FIG. 1, which has a height which extends between the top surface 18 of the holder body to adjacent to and planar with the lower planar bases of the respective chambers.

In an alternative embodiment, the through passageway 22 may be a through slit which has a height that extends only part of the distance between the top surface of the holder body and the lower planar bases of the respective chambers.

In certain embodiments, the through slit is approximately 2 mm wide and approximately 4 mm in length. In other embodiments, the through slit is approximately 2 mm wide and approximately 3.5 mm in length. Other dimensions of the through slit are envisaged.

In a yet further embodiment, the through passageway 22 is a through hole which is provided between the side wall 16*a* of the first chamber 12*a* and the side wall 16*b* of the second chamber 12*b*. The through hole may be provided at a lower portion of the respective side walls.

The through passageway should be sized so as to allow fluid movement between the respective adjacent chambers. Such fluid includes for example liquid cell culture media. The cell culture media may comprise a plurality of components including for example components secreted by cells and/or tissues provided within one or both chambers. Thus, the through passageway allows for an exchange of cell culture media and components comprised therein between chambers of the multi-well plate apparatus.

In the illustrated embodiment, a through passageway is provided between two adjacent chambers. It will be understood that in certain embodiments a through passageway may be provided between three or more chambers. Aptly, the through passageway comprises a plurality of through slits and/or through holes, a first slit or hole being provided between a side wall or base of a first chamber and an adjacent second chamber, and further slits and/or holes being provided between the first or second chamber and adjacent further chamber and optionally between adjacent further chambers. In such embodiments, the through passageway is provided in a linear non-angled direction between the plurality of chambers.

The holder body further comprises an outer perimeter wall 24. The outer perimeter wall may comprise a recessed outer edge portion 26 which provides a surface 28. The lower planar surface of the holder body may comprise a recessed edge region (not shown) which is configured to rest and locate on the surface 28 of the recessed outer edge portion of a further holder body such that the holder bodies are located in a nested relationship. In certain embodiments, a plurality of holder bodies may be located in a vertical nested relationship.

In certain embodiments, the apparatus also comprises one or more insert elements 30 which are configured to support one or more cells. In certain embodiments, the insert element may be a TRANSWELL® permeable support available from Corning, US. The cells may be in the form of a tissue portion e.g. a tissue slice. The insert element may provide a 3D cell scaffold. As shown in FIG. 4, the insert element 30 has a body portion 32 which is generally cylindrical in shape. The insert element is sized so as to fit within a chamber. The insert element also comprises a plurality of radially outwardly extending flanges 34*a*, 34*b*, 34*c* which, when the insert element is placed in a chamber, contact and rest on the top surface of the holder body so as to support the insert element within the chamber.

Aptly, when supported by the flanges resting on the top surface, the insert element is positioned within the chamber such that it does not contact a side wall or the base of the chamber. As a result, when the chamber is filled with fluid e.g. cell culture media, the insert element is at least partially surrounded by the fluid. In other embodiments, the insert element may contact the base of the chamber for example. The insert element may comprise a lower surface membrane 40 with pores.

Aptly, the pores having an average diameter of between about around 8 μm to about 150 μm. in one embodiment, the pores have an average diameter of about 8 μm. The insert element may be coated with a matrix material e.g. collagen or the like.

In use, the top surface of the holder body may be covered by a common removable lid (not shown). The lid may be removed to add or remove components in the chambers such as cell inserts, cell scaffolds, cell culture media, and the like.

Turning to FIGS. 3 and 5, a rocker apparatus 100 according to certain embodiments of the present invention is illustrated.

FIG. 3*a* represents an apparatus for providing bi-directional fluid flow and which includes a rocker apparatus holding a multi-well plate apparatus according to certain embodiments of the present invention. As illustrated by arrows, media exchange may occur via insert pores within wells of the plate apparatus. In addition, bi-directional media exchange may occur via a channel between wells. A tissue slice is illustrated in the chambers in FIG. 3*a*.

The rocker apparatus may be alternatively referred to as a "see-saw" type apparatus. A schematic representation of the rocker apparatus 100 is shown in FIG. 5. The rocker apparatus comprises a holder body support 102 which directly or indirectly supports a holder body 10. Aptly, the holder body support includes a fixed pivot or fulcrum on which a is moveable platform 104 is supported. The platform 104 includes an upper surface for supporting the holder body 10. The platform and fixed pivot can be formed from any suitable material including for example plastic, metal or wood. The platform comprises a first end region 106 and a second end region 108 spaced apart from the first end.

The rocker apparatus 100 may be configured to tilt the platform 104 e.g. by raising and lowering spaced apart end regions. Aptly, the platform 104 is biased downwardly at one of the spaced apart end regions e.g. by way of a weight which is provided at the respective end region. The weighted end is biased downwards to a resting position. Aptly, the bias is a minimal bias which is just sufficient to overcome the weight of the opposing end region.

The apparatus 100 also comprises a drive element arranged to rock the holder body supported via the support to thereby repeatedly raise and lower the spaced apart first and second ends of the holder body. In one embodiment, the rocker apparatus comprises a drive element comprising a linear actuator 110 provided at the first end region 106. In one particular embodiment, a linear actuator is configured to tilt the platform, and therefore the multi-well plate. Under normal circumstances therefore this end of the platform will rest lower. The actuator is arranged to drive against the base, so that when driven it raises that end of the platform and lowers the other spaced apart end.

In some embodiments, the linear actuator provides the biasing weight itself and so can be used to return the platform passively to its resting position with first end 106 lowered, such that the drive element need only drive actively in one direction.

In one particular embodiment, the linear actuator is configured to tilt the platform, and therefore the multi-well plate, at a speed of between about 10 seconds to about 20 minutes e.g. about 2 minutes per rock i.e. approximately two minutes for the first end of the holder body to be moved from a first position e.g. a lowered position to a second position e.g. a raised position.

The linear actuator may be powered by battery or by mains power for example.

It will be appreciated that FIG. 5 is a schematic representation only and the angle of tilt of the platform may be smaller than depicted in FIG. 5. For example, the platform may have a range of tilt from 0 degrees to about +/−20 degrees or less e.g. 1, 2, 3, 4, 5, 6, 7, 8, 9, 10, 11, 12, 13, 14, 15, 16, 17, 18, 19 or 20 degrees.

The tilting action of the rocker apparatus enables fluid e.g. liquid cell culture media to flow from a first chamber, via the fluid communication pathway, to a second chamber and back again. In certain embodiments, e.g. when each chamber has a well diameter of approximately 20 mm, the rocking of the holder body enables fluid to flow between adjacent chambers at a rate of between about 15 to about 20 μl/second via the through passageway. In certain embodiments, at all stages of the rocking motion, a cell or tissue culture provided within a chamber remains at least partially covered by the cell culture media.

Rocking not only allows media exchange between the two chambers but also permits media exchange via the pores in the culture insert membrane which separate the inner and outer wells. The latter media exchange generates flow around/over a tissue slice, which will aid oxygenation and removal of toxic metabolites, which in turn is likely to increase viability and function of the tissue.

The multi-well plate and rocker apparatus as described herein can be used in a variety of methods to provide a dynamic cell culture environment which may more accurately represent in vivo conditions and therefore better support the growth and maintenance of cells and/or tissues in culture.

Figure 30:
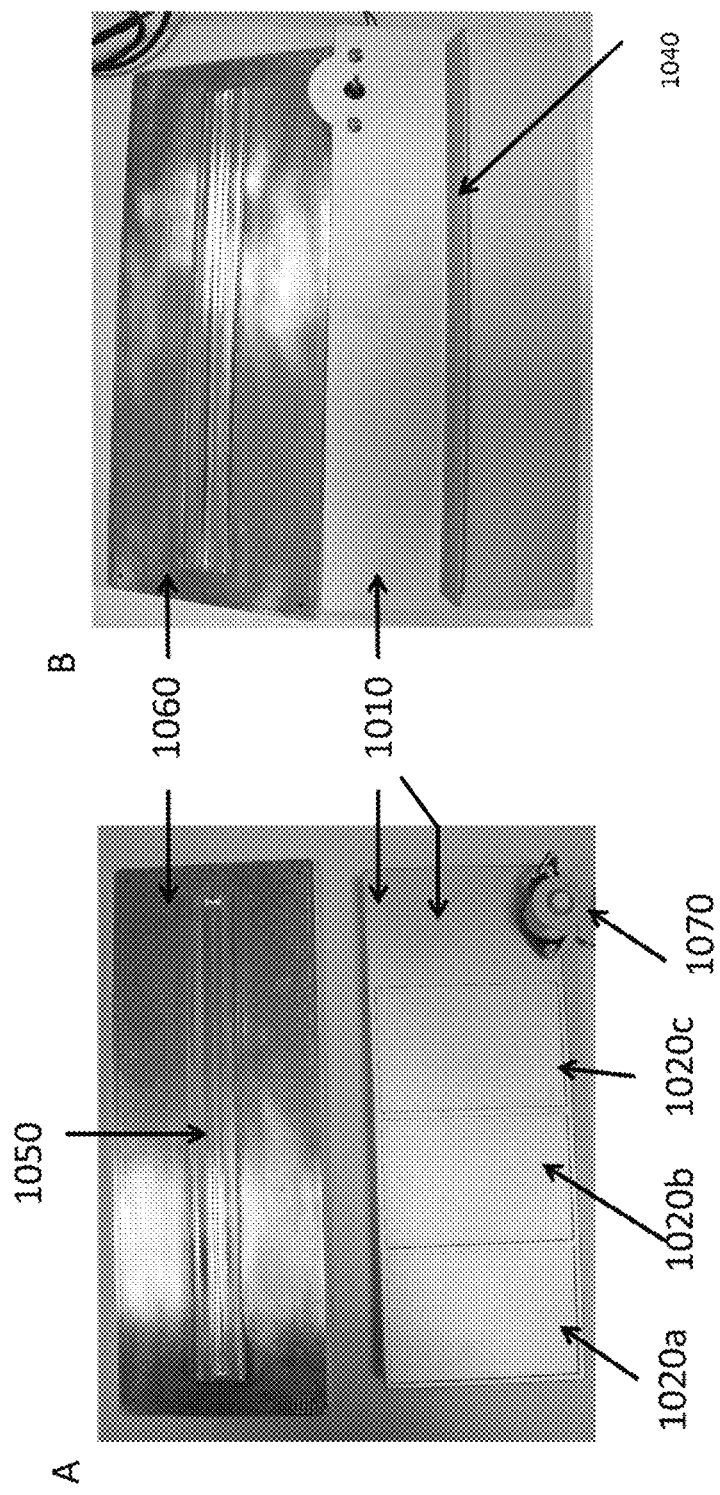

FIG. 29 depicts an apparatus 1000 according to certain embodiments of the invention, while FIG. 30 depicts elements thereof. The apparatus 1000 includes a platform element 1010 which is configured to support a plurality of culture apparatus or multi-well plates as described herein. The platform may comprise a plurality of recessed regions 1020*a*, 1020*b*, 1020*c* which are each sized to locate a multi-well plate. A lip region 1030 is provided which extends substantially around the periphery of the platform and separates each recessed region. The lip region acts to prevent the culture apparatus from sliding when the apparatus is being rocked. In some embodiments, a plurality of multi-well plates may be stacked as shown in FIG. 29.

The apparatus 1000 comprises a pivot element 1040 which sits in a central groove 1050 which is provided in a base portion 1060 of the apparatus. The linear actuator 1070 moves the platform up and down about the pivot element 1040 to tilt the culture apparatus up and down as described above.

Certain embodiments of the present invention relate to a method of culturing cells and/or tissues as described herein below:

EXAMPLES

Hepatocytes often present a challenge in cell culture and are known to rapidly loose phenotypic expression in vitro due to the absence of a suitable microenvironment. The following examples focussed on determining whether the apparatus of certain embodiments of the present invention could be used to prevent or delay phenotypic expression loss in hepatocytes. The term "CMR", "CMR2" and "CMR tissue culture plates" used herein refers to the plate apparatus of certain embodiments of the present invention.

Precision Cut Slice Isolation and Culture

Liver tissue was placed in a 10 cm dish containing Hanks Buffered Saline Solution (HBSS+, Lonza, BD10-508F). Four to eight mm cores of liver tissue were made using a Stiefel Biopsy Punch. Cores were then transferred to a metal mould and submerged in 2.5-3.0% low gelling temperature agarose (Sigma, A9414) and then placed on ice for 2-5 minutes.

Once set, the cores in agarose were super-glued to a vibratome mounting stage and submersed in the media chamber in ice cold HBSS+ prior to cutting on a Leica VT1200 S fully automated vibrating blade microtome. Liver tissue cores were cut at a speed of 0.3 mm/sec, and an amplitude 2 mm and thickness (step size) of 250 μm. Slices having a thickness of between 200-400 μm can be used.

Slices were transferred to 3 μm, 8 μm or 100 μm pore inserts provided in static (Griener) or CMR tissue culture plates. The CMR tissue culture plates of embodiments of the invention comprised either holes between adjacent wells or were rapid prototyped from CAD design to comprise slots between wells. The wells contained slice culture media. The slices were cultured under static, unidirectional or rocked conditions at 37° C. in 5% carbon dioxide in a humidified tissue culture incubator. Twelve or twenty-four well CMR tissue culture plates were used, as indicated.

Slice Culture Media

The slice culture media comprised the following components:

Williams Medium E (Sigma, W4128)
2% Heat Inactivated Fetal Bovine Serum (Gibco)
Penicillin-Streptomycin (Sigma, P0781)
L-glutamine (Sigma, G7513)
Pyruvate (Sigma, S8636)
0.5 uM Insulin/transferrin selenium mix (Gibco 51500-056)
0.1 uM dexamethasone (Sigma, D4902)

Urea Assay (Universal Biologicals Cambridge)

50 μl of the slice culture media from slices in static or CMR culture was used to quantify urea release using the QuantiChrom™ Urea Assay Kit (catalogue number DIUR-500) following manufacturer's instructions.

Albumin Elisa (Bethyl Laboratories)

100 μl of the slice culture media diluted 1:250 was removed from wells comprising slices in either a static culture plate, a unidirectional system or the CMR culture plate apparatus which was rocked using a rocking apparatus as described herein. The media was used to quantify albumin release using the Rat Albumin ELISA Quantitation Set (catalogue number E110-125) or Human Albumin ELISA Quantitation Set (catalogue number E80-129) following manufacturer's instructions.

LDH Cytotoxicity Assay Kit (Pierce)

50 μl media was removed from wells comprising slices in either a static culture plate or the CMR culture plate apparatus which was rocked using a rocking apparatus as described herein. The media was used to quantify lactate dehydrogenase release (LDH) release using the LDH Cytotoxicity Assay Kit (catalogue number 88953) following manufacturer's instructions.

Aspartate Aminotransferase (AST)

200 μl media from slices in static or CMR culture was sent to the Clinical pathology department, Royal Victoria infirmary, Newcastle Upon Tyne. AST was measured using a clinical colorimetric enzyme assay.

Results are shown in FIGS. 6 to 28 and 31 to 32.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A multi-well plate apparatus for providing bi-directional fluid flow for culturing cells within the plate apparatus, comprising:
    a holder body;
    a holder body support;
    at least one drive element arranged to rock a holder body supported via the support to thereby repeatedly raise and lower spaced apart ends of the holder body, wherein the apparatus for providing bi-directional fluid flow is configured to repeatedly rock the holder body; and
    wherein the holder body comprises a plurality of pairs of adjacent chambers, each pair of adjacent chambers comprising:
        a first chamber containing a first base element;
        a second chamber containing a second base element; and
        a channel extending between the interior of the first chamber and the interior of the second chamber; and
    a plurality of insert elements, each disposed within an individual chamber;
    wherein:
        each channel permits bi-directional fluid flow between only the first chamber and the second chamber of each pair of adjacent chambers;
        each chamber is directly connected to the only one channel;
        the width of each channel is 1.5 mm-3.5 mm; and
        the height of each channel extends between a top surface of the holder body and the first and second base elements;
    wherein the apparatus is configured to enable bi-directional fluid flow between the first chamber and the second chamber at a rate of between about 15 to about 20 μl per second.

2. The apparatus of claim 1, wherein the volume of each pair of adjacent chambers, including the channel, is between 0.5 mL and 8 mL.

3. The apparatus of claim 1, wherein each chamber comprises at least one side wall element.

4. The apparatus of claim 3, wherein each channel extends between a base or side wall of the first chamber to a base or side wall of the second chamber of each pair of adjacent chambers.

5. The apparatus of claim 1, wherein each insert element further comprises a plurality of radially extending flanges which contact and rest on a top surface of the holder body, supporting the insert element within a chamber.

6. The apparatus of claim 5, wherein the flanges position the insert element within a chamber such that is does not contact a side wall or base of the chamber.

7. The apparatus of claim 1, wherein each insert element is configured to support a cell scaffold element comprising a porous lower surface membrane, wherein the average diameter of the ports is 8 μm-150 μm.

8. The apparatus of claim 1, wherein the at least one drive element is configured to rock the holder body at a speed of approximately 1 minute-20 minutes per complete rocking motion.

9. The apparatus of claim 1, wherein:
    (a) the holder body comprises at least six pairs of adjacent chambers;
    (b) the holder body further comprises an outer perimeter wall element, wherein the outer perimeter wall element comprises an inwardly stepped portion configured to allow a plurality of holder bodies to be vertically stacked;
    (c) the apparatus further comprises a lid element which is removably positionable over the holder body, the lid element providing a substantially planar cover extending over the plurality of chambers; or
    (d) the pairs of adjacent chambers are arranged in rows and columns in a respective orthogonal relationship within the holder body.

10. The apparatus of claim 9, wherein each respective chamber of the plurality of chambers has a depth of 16 mm-19 mm.

11. The apparatus of claim 1, wherein:
    each insert element further comprises a lower surface; and
    the lower surface of each insert element is positioned such that there is a space defined between the lower surface of each insert element and the base element of the chamber into which each insert element is disposed.

12. The apparatus of claim 1, wherein the at least one drive element is configured to enable bi-directional fluid flow between the first chamber and the second chamber at a rate of between about 15 to about 20 µl per second.

13. The apparatus of claim 1, wherein each channel is a through passageway configured to provide a fluid communication pathway between the interior of the first chamber and the interior of the second chamber.

* * * * *